US007601525B2

(12) United States Patent
Batich et al.

(10) Patent No.: US 7,601,525 B2
(45) Date of Patent: Oct. 13, 2009

(54) ALGINATE GEL SCAFFOLD HAVING A PLURALITY OF CONTINUOUS PARALLEL MICROTUBULAR COPPER CAPILLARIES

(75) Inventors: Christopher D. Batich, Gainesville, FL (US); Bradley Jay Willenberg, Gainesville, FL (US); Takashi Hamazaki, Gainesville, FL (US); Naohiro Terada, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 349 days.

(21) Appl. No.: 11/074,285

(22) Filed: Mar. 7, 2005

(65) Prior Publication Data

US 2005/0196423 A1 Sep. 8, 2005

Related U.S. Application Data

(60) Provisional application No. 60/550,910, filed on Mar. 5, 2004.

(51) Int. Cl.
*C12N 11/10* (2006.01)
*C12N 11/04* (2006.01)
*C12N 5/02* (2006.01)
(52) U.S. Cl. .................... 435/178; 435/182; 424/93.7
(58) Field of Classification Search ................ None
See application file for complete search history.

(56) References Cited

U.S. PATENT DOCUMENTS

| 4,348,418 | A |   | 9/1982 | Smith et al. |
| 5,563,186 | A |   | 10/1996 | Thompson |
| 5,575,815 | A |   | 11/1996 | Slepian et al. |
| 5,709,854 | A |   | 1/1998 | Griffith-Cima et al. |
| 5,762,959 | A | * | 6/1998 | Soon-Shiong et al. ....... 424/451 |
| 6,599,323 | B2 | * | 7/2003 | Melican et al. .......... 623/23.72 |
| 6,761,887 | B1 |   | 7/2004 | Kavalkovich et al. |

FOREIGN PATENT DOCUMENTS

WO WO 03/041758 A1 5/2003

OTHER PUBLICATIONS

Willenberg, B. et al. "Self-assembled copper-capillary alginate gel scaffolds with oligochitosan support embryonic stem cell growth" *J. Biomed. Mater. Res.*, 2006, 79:440-450.
Mosahebi, A. et al. "A novel use of alginate hydrogel as Schwann cell matrix" *Tissue Engin.*, 2001, 7:525-534.
Treml, H. et al. "Theory of capillary formation in alginate gels" *Chemical Physics*, 2003, 293:341-353.
Bartkowiak, A. and Hunkeler, D. "New microcapsules based on oligoelectrolyte complexation" *Ann. N.Y. Acad. Sci.*, 1999, 875:36-45.
Gaserod, O. et al. "Microcapsules of alginate-chitosan. II. A study of capsule stability and permeability" *Biomaterials*, 1999, 20(8):773-783.

Hassan, R.M. et al. "Separation of metal alginate ionotropic gels to polymembranes with special evidence on the position of chelation in copper alginate complex" *Journal of Polymer Science*, 1991, 29(11):1645-1648.
Hassan, R.M. at al. "Kinetics and mechanism of sol-gel transformation for polyelectrolytes of capillary copper alginate ionotropic membranes" *European Polymer Journal*, 1988, 24(12):1173-1175.
ISP Alginates, Section 3: Algin-Manufacture and Structure, in *Alginates: Products for Scientific Water Control*, 2000, International Specialty Products: San Diego, pp. 4-7.
Kataoka, K. et al. "Alginate, a bioresorbable material derived from brown seaweed, enhances elongation of amputated axons of spinal cord in infant rats" *J. Biomed. Mater. Res.*, 2001, 54:373-384.
Kuo, C.K. and MA, P.X. "Ionically crosslinked alginate hydrogels as scaffolds for tissue engineering: Part 1. Structure, gelation rate and mechanical properties" *Biomaterials*, 2001, 22(6):511-521.
McBeath, R. et al. "Cell shape, cytoskeletal tension, and RhoA regulate stem cell lineage commitment" *Developmental Cell*, 2004, 6:483-495.
Murata, Y et al. "Preparation of chitosan-reinforced alginate gel beads—effects of chitosan on gel matrix erosion" *International Journal of Pharmaceutics*, 1993, 96:139-145.
Ouwerx, C. at al. "Physico-chemical properties and rheology of alginate gel beads formed with various divalent cations" *Polymer Gels and Networks*, 1998, 6(5):393-408.
Schuberth, R. *Ionotropic Copper Alginates: Investigations into the formation of capillary gels and filtering properties of the primary membrane*, 1992, University of Regensburg: Regensburg.
Schuberth, R. *Ionotropic Copper Alginates: Investigations into the formation of capillary gels and filtering properties of the primary membrane*, 1992, University of Regensburg: Regensburg; English-language translation.
Suzuki, K. et al. "Regeneration of transected spinal cord in young adult rats using freeze-dried alginate gel" *Neuroreport*, 1999, 10(14):2891-2894.
Suzuki, Y. et al. "Spinal cord regeneration through alginate, a polysaccharide from seaweed" *European Journal of Neuroscience*, 2000, 12:287, abstract No. 129.07.
Thiele, H. "Histolyse und Histogenese" published in 1967 by Akademische Verlagsgesellschaft, pp. 1-157.
Thiele, H. "Histolyse und Histogenese" published in 1967 by Akademische Verlagsgesellschaft, pp. 1-157, English-language translation.
Thu, B. et al. "Alginate gels—some structure-function correlations relevant to their use as immobilization matrix for cells" *Progress in Biotechnology*, 1996, 11:19-30.
Thumbs, J. and Kohler, H-H. "Capillaries in alginate gel as an example of dissipative structure formation" *Chemical Physics*, 1996, 208(1):9-24.
Yan, X.L. et al. "PEC films prepared from chitosan-alginate coacervates" *Chem. & Pharm. Bull.*, 2000, 48(7):941-946.

(Continued)

*Primary Examiner*—David M Naff
(74) *Attorney, Agent, or Firm*—Saliwanchik, Lloyd & Saliwanchik

(57) ABSTRACT

The present invention provides copper capillary alginate gels stabilized with barium, chitosan, its derivates, or a combination thereof. These stabilized gels are useful as scaffolds for containing, growing, or regenerating biological agents and cells for in vivo or in vitro use.

31 Claims, 28 Drawing Sheets

OTHER PUBLICATIONS

Börner, A. et al. "Alginate/calcium phosphate scaffolds with oriented, tube-like pores" 7th Essen Symposium on Biomaterials and Biomechanics: Fundamentals and Clinical Applications Oct. 6-8, 2004, University Duisburg-Essen, Campus Essen.

Guertin, D. and Sabatini, D. "Cell size control" *Encycl. Life Sci.*, 2005, pp. 1-10.

Despang et al. "Alginate/calcium phosphate scaffolds with oriented, tube-like pores" *Materialwiss Werkstofftech*, 2005, pp. 761-767, vol. 36, No. 12.

Laffafian, I. and Hallett, M.B. "Lipid-assisted microinjection: Introducing material into the cytosol and membranes of small cells" *Biophysical Journal*, 1998, 75:2558-2563.

Dittrich et al. "Mineralized scaffolds for hard tissue engineering by ionotropic gelation of alginate" *Adv Sci Technol Mater Clin* Appl, 2006, pp. 159-164, vol. 49.

Suzuki et al., "Reconstruction of rat peripheral nerve gap without sutures using freeze-dried alginate gel" *Journal of Biomedical Materials Research*, 2000, epub Dec. 1999, pp. 528-533, vol. 49, No. 4.

Suzuki, et al., "Cat peripheral nerve regeneration across 50 mm gap repaired with a novel nerve guide composed of freeze-dried alginate gel" *Neuroscience Letters*, 1999, pp. 75-78, vol. 259, No. 2.

Xu et al. "Preparation and characterization of alginate hydrogel membranes crosslinked using a water-soluble carbodiimide" *Journal of Applied Polymer Science*, 2003, pp. 747-753, vol. 90, No. 3.

\* cited by examiner

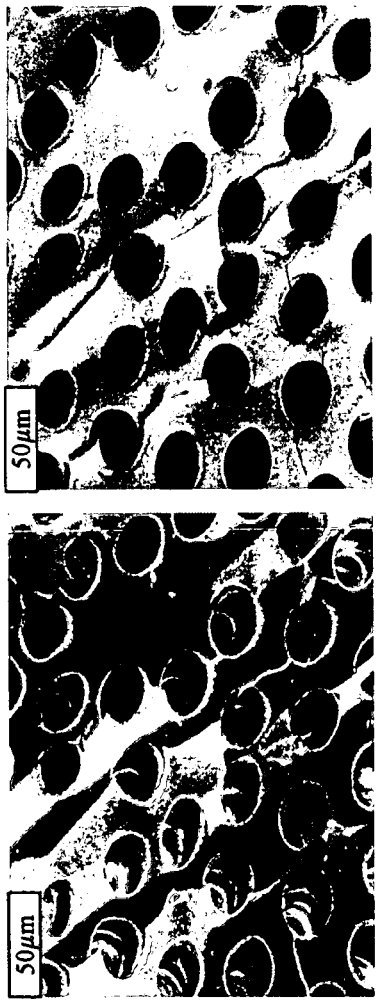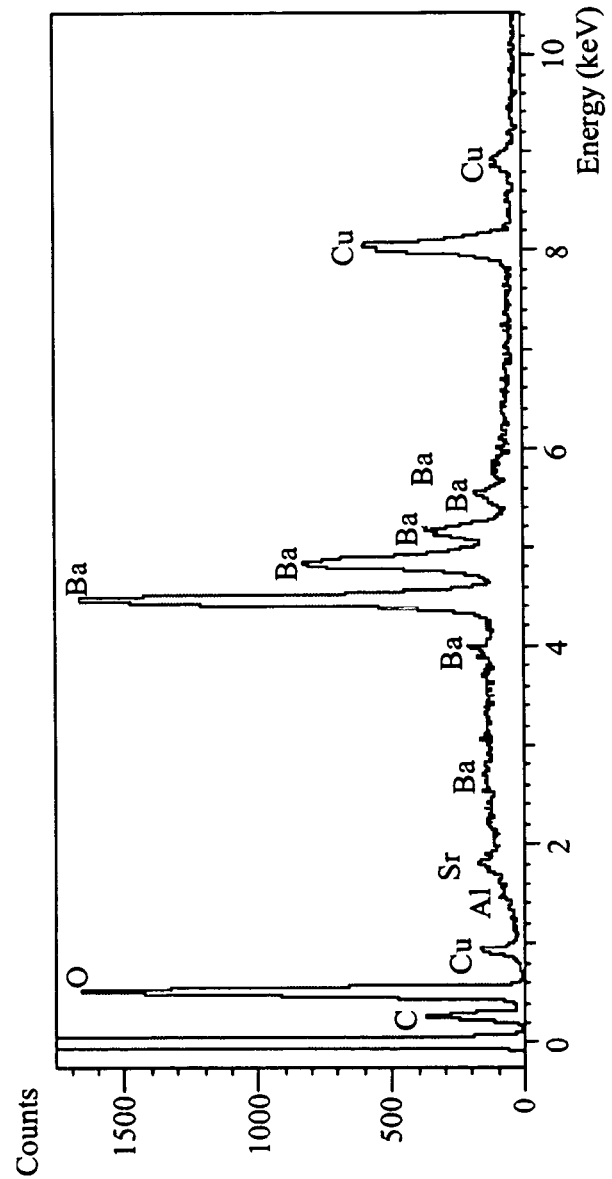
FIG. 15A
FIG. 15B
FIG. 15C

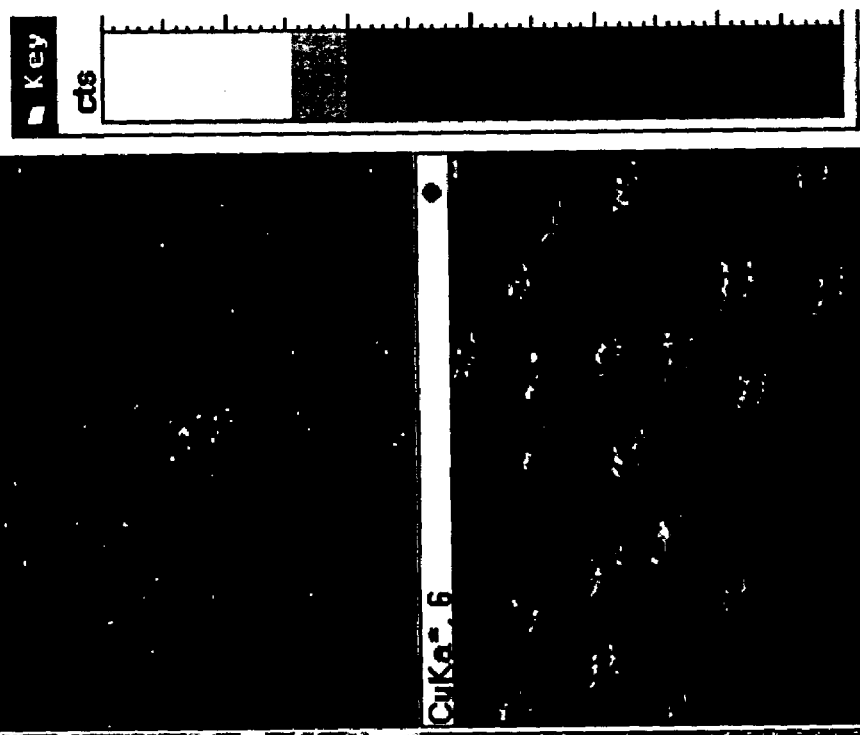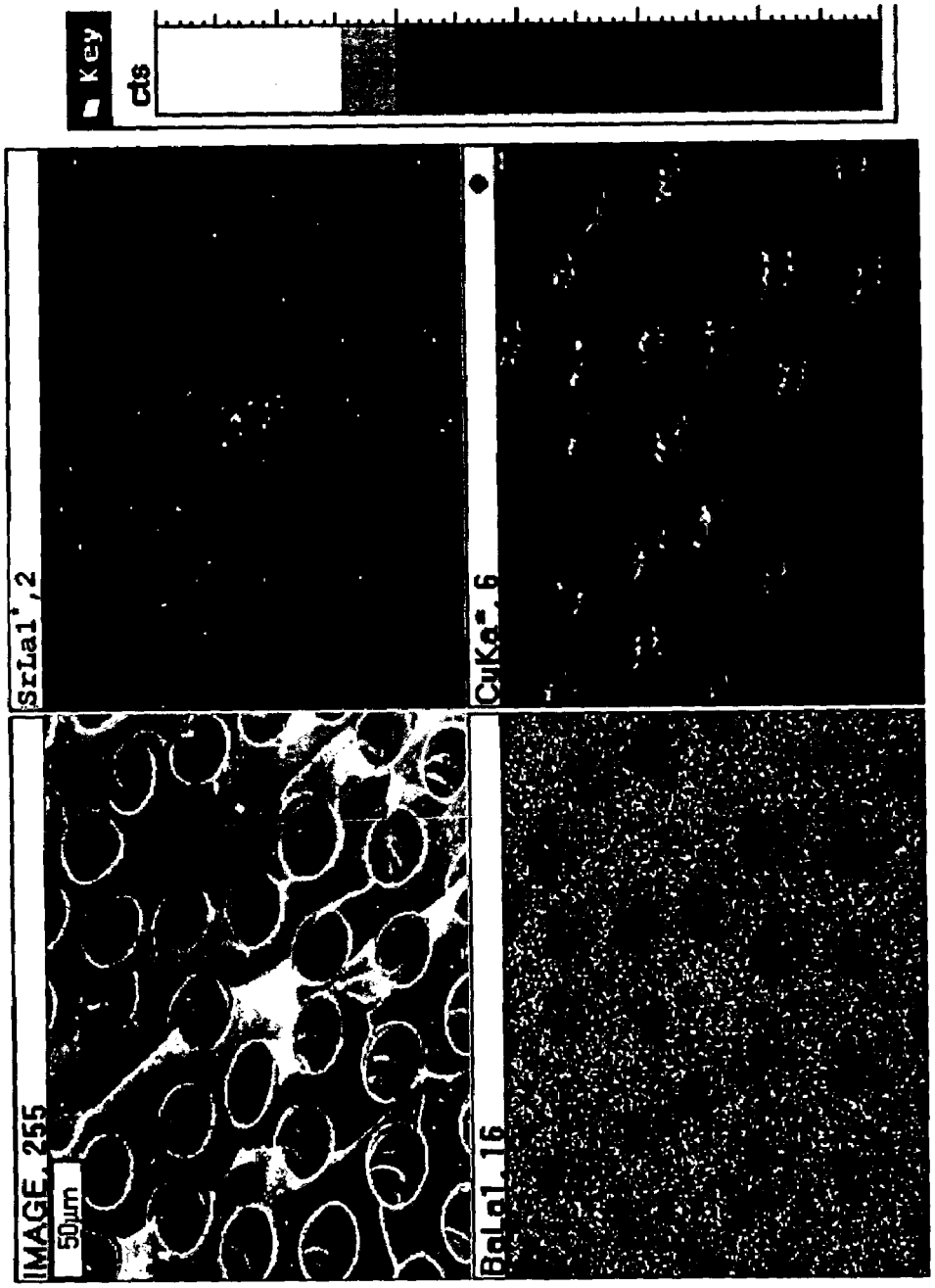
FIG. 15E  FIG. 15G  FIG. 15D  FIG. 15F

ALGINATE GEL SCAFFOLD HAVING A PLURALITY OF CONTINUOUS PARALLEL MICROTUBULAR COPPER CAPILLARIES

CROSS-REFERENCE TO RELATED APPLICATION

The present application claims benefit of U.S. Provisional Application Ser. No. 60/550,910, filed Mar. 5, 2004, which is hereby incorporated by reference herein in its entirety, including any figures, tables, nucleic acid sequences, amino acid sequences, and drawings.

FIELD OF THE INVENTION

The present invention relates to copper capillary alginate gels stabilized with at least one agent so that the gel is stable in fluid and biological environments and methods of preparation and use.

BACKGROUND OF THE INVENTION

Nerves are composed of motor, sensory and sympathetic components (Evans, G. R. D., *Anatomical Record*, 2001, 263(4):396-404). Nerves may be designated as primarily motor or sensory; however, no nerve is purely one or the other (Evans, G. R. D., *Anatomical Record*, 2001, 263(4):396-404). Myelinated and unmyelinated axons comprise the nerve fibers. Motor fibers are primarily myelinated and are outnumbered by unmyelinated sensory fibers 4:1 (Evans, G. R. D., *Anatomical Record*, 2001, 263(4):396-404). Myelinated fibers range in size from 1-20 µm in diameter while umyelinated fibers are typically below 1 µm in diameter (Carpenter, M. B., *Human Neuroanatomy*, 1979, p. 71-114 and 188-190; Cajal, S. R., *Chapter IX: Nerve Fibers*, in *Histology of the Nervous System*, 1995, p. 209-235).

Nerves carry the peripheral processes or axons of neurons but also consist of Schwann cells and connective tissue sheaths. The most inner sheath, the edoneurium, is composed mainly of longitudinally aligned collagen fibers 30-60 nm in diameter (Carpenter, M. B., *Human Neuroanatomy*, 1979, p. 71-114 and 188-190; Ross, M. et al., Ch 11: *Nervous Tissue*, in *Histology: A Text and Atlas*, 1989, p. 241-281; Peters, A. et al., Ch. 12: *Connective Tissue Shealths of Peripheral Nerves*, in *The Fine Structure of the Nervous System—Neurons and Their Supporting Cells*, 1991, p. 384-394). Tiny capillaries (<10 µm), fibroblasts, mast cells and macrophages are also found in the endoneurium. The innermost endoneurial layer is often observed to be in close contact with Schwann cell basal laminae.

The perineurium layer comprises cells that exhibit both myoid and epithelioid features and express basal lamina on both surfaces (Carpenter, M. B., *Human Neuroanatomy*, 1979, p. 71-114 and 188-190; Ross, M. et al., Ch 11: *Nervous Tissue*, in *Histology: A Text and Atlas*, 1989, p. 241-281; Peters, A. et al., Ch. 12. *Connective Tissue Shealths of Peripheral Nerves*, in *The Fine Structure of the Nervous System—Neurons and Their Supporting Cells*, 1991, p. 384-394). The cells are interlocked in successive sheets via tight junctions. Blood vessels also infiltrate this layer with the perineurim functioning as a selectively permeable barrier. The outermost perineurial layers are composed of dense concentric layers of mostly longitudinally arranged collagen fibrils ca. 50 nm in diameter with a few fibroblasts and macrophages among the strands.

The outer sheath, the epineurium layer, is a dense collagenous layer surrounding all peripheral nerve trunks (Carpenter, M. B., *Human Neuroanatomy*, 1979, p. 71-114 and 188-190; Ross, M. et al., Ch 11: *Nervous Tissue*, in *Histology: A Text and Atlas*, 1989, p. 241-281; Peters, A. et al., Ch. 12: *Connective Tissue Shealths of Peripheral Nerves*, in *The Fine Structure of the Nervous System—Neurons and Their Supporting Cells*, 1991, p. 384-394). Fibers in this layer are disposed mainly longitudinally with diameters between 70-85 nm. Elastin fibers are also present with diameters ranging from 250-500 nm. Fibroblasts and mast cells are scattered throughout this layer.

In most tissues, wound healing is usually a coordinated sequence of events that includes (a) tissue disruption and loss of normal tissue architecture; (b) cell necrosis and hemorrhage; hemostasis (clot formation); (c) infiltration of segmented and mononuclear inflammatory cells, with vascular congestion and tissue edema; (d) dissolution of the clot as well as damaged cells and tissues by mononuclear cells (macrophages); and (e) formation of granulation tissue (fibroplasia and angiogenesis). This sequence of cellular events has been observed in wounds from all tissues and organs generated in a large number of mammalian species (See Berry et al., In: *CNS Injuries: Responses and Pharmacological Strategies*, 1998, A. Logan and M. Berry, eds., CRC Press, Boca Raton, Fla.; Gailet et al., *Curr. Opin. Cell. Biol.*, 1994, 6:717-725). Therefore, the cellular sequence described above is a stereotype of the repair of all mammalian tissues.

Peripheral nerve injuries are extremely prevalent. Each year, an estimated 50,000 peripheral nerve repair procedures are performed in the United States alone (Evans, G. R. D., *Anatomical Record*, 2001, 263(4):396-404). Much of what has been learned about peripheral nerve repair has grown out of the treatment of warfare injuries (Neal, N., *Military Contributions to Peripheral Nerve Injuries*. Gray Matters: Newsletter of the National Capital Neurosurgery Program, 2000: p. 1-5). Unfortunately, despite many advances and creative repair strategies, the functional outcomes of nerve repairs are still far from optimal and motor nerves tend to be more refractory than sensory to full recovery (Evans, G. R. D., *Anatomical Record*, 2001, 263(4):396-404).

Peripheral nerve injury may result from trauma (e.g., lacerations, gunshot wounds, motor vehicle accidents), acute compression, stretching/tension or disease (e.g., cancer, leprosy). A five category system classifies nerve injuries in terms of increasing severity from first-degree to fifth-degree (Evans, G. R. D., *Anatomical Record*, 2001, 263(4):396-404). A first-degree injury or neurapraxia involves a temporary conduction block with local demyelination yet complete recovery occurs.

Axotomy (axon severance) occurs after any 2nd degree injury or higher. The more severe traumas often require surgery for a chance for complete or partial recovery. When transected or resected nerve ends can not be coapted without tension, a gap defect results requiring nerve grafting to restore neural continuity (Kline, D., et al., *Chapter XXV: Graft Repair*, in *Atlas of Peripheral Nerve Surgery*, 2001, p. 183-187).

Autograft (autologous nerve) is the "gold standard" graft material and is preferentially obtained from harvest of the sural nerve, antebrachial cutaneous radial nerve or superficial sensory radial (SSR) nerve (Kline, D., et al., *Chapter XXV: Graft Repair*, in *Atlas of Peripheral Nerve Surgery*, 2001, p. 183-187). The fundamental determinates of functional regeneration for autograft are the endoneurium and remaining Schwann cells since the epineural and perineural elements are trimmed from harvested nerve prior to engraftment.

Although autograft is reported to facilitate neuroregeneration over substantial distances (2-15 cm) (Meek, M. F. and J.

H. Coert, *Journal of Reconstructive Microsurgery*, 2002, 18(2):97-109), it has some disadvantages. Lack of donor supply, donor site morbidity, need for secondary surgical site and insufficient functional outcome are the key disadvantages of autograft repair (Hadlock, T. et al., *Archives of Otolaryngology-Head & Neck Surgery*, 1998, 124(10):1081-1086; Evans, G. R. D., *Anatomical Record*, 2001, 263(4):396-404; Meek, M. F. and J. H. Coert, *Journal of Reconstructive Microsurgery*, 2002, 18(2):97-109). Harvesting donor nerve is also time-consuming and often the fascicles do not match the target nerve in both number and diameter. Central or segmental necrosis can also occur in large diameter grafts (Terzis, J. K. et al., *International Angiology*, 1995, 14(3):264-277). Thus, there exists a need for neuroregenerative conduits constructed from both natural and synthetic materials to supplant autograft.

Entubulation is the most common alternative to autograft repair (Mackinnon, S. E., *Journal of Reconstructive Microsurgery*, 2001, 17(8):596-597). In this strategy, severed nerve ends are inserted into the hollow or filled lumen of a biomaterial tube employed to protect, facilitate and guide neuroregeneration. Gaps of centimeters have been regenerated successfully, dependent upon the specific materials employed (Langer, R. and J. P. Vacanti, *Tissue Engineering. Science*, 1993, 260(5110):920-926; Strauch, B. et al., *Journal of Reconstructive Microsurgery*, 2001, 17(8):589-595; Meek, M. F. and J. H. Coert, *Journal of Reconstructive Microsurgery*, 2002; DenDunnen, W. F. A. et al., Microsurgery, 1996, 17(7):348-357; Suzuki, K. et al., *Journal of Biomedical Materials Research*, 1999, 49(4):528-533; Suzuki, Y. et al., *Neuroscience Letters*, 1999, 259(2):75-78; Chen, Y. S. et al., *Biomaterials*, 2000, 21(15):1541-1547; Battiston, B. et al., *Microsurgery*, 2000, 20(1):32-36; Shen, Z. L. et al., *Microsurgery*, 2001, 21(1):6-11; Gulati, A. K. et al., *Brain Research*, 1995, 705(1-2): 118-124; Evans, G. R. D. et al., *Biomaterials*, 1999, 20(12): 1109-1115).

Vein, denatured muscle, combination vein filled with muscle, silicone, Gore-Tex, and polyglycolic acid (PGA) tubes have been used clinically in humans for nerve reconstruction with success (Meek, M. F. and J. H. Coert, *Journal of Reconstructive Microsurgery*, 2002). Vein grafts were found suitable for gap lengths of less than 4.5 cm dependent upon the nerve under repair. Muscle grafts appeared suitable for reconstruction of gaps greater than 6 cm in leprosy patients and were judged superior to conventional nerve grafting in repair of 1.5-2.8 cm gaps resulting from laceration injuries. Combination vein filled with muscle conduits have been used to successfully reconstruct 6 cm gaps. The ready supply of vein and muscle make them attractive graft material choices, and combination vein-muscle grafts have shown superior results to vein alone in similar defects.

Hollow GORE-TEX conduits are indicated in reconstructions up to 4 cm and cause less tissue irritation than silicone tubes. Silicone tubes have only shown success for 4 mm gaps and 29% of the tubes needed to be removed due to (compressive) irritation. In clinical studies utilizing PGA tubes, the maximum defect that could be reconstructed was 3 cm and the conduits performed significantly better than autograft. Allografts in combination with systemic immunosuppressive therapy have also been used successfully in the clinic to reconstruct massive (>10-20 cm) peripheral nerve defects although the accompanying therapy is a serious drawback (Mackinnon, S. E. et al., *Plastic and Reconstructive Surgery*, 2001, 107(6):1419-1429).

Although clinical studies demonstrate that conduits, natural or synthetic, are at least comparable to autograft in repair of short defects ($\leq$ca. 3 cm), there still exists a need for a conduit or scaffold useful for repairing large nerve gaps, such as a bioresorbable synthetic conduit capable of holding permissive tissues.

Biomaterial scaffolds are a fundamental component of tissue reparative, restorative and regenerative strategies, and development of advanced biomaterial scaffolds is crucial to the continued progress and success of the tissue engineered field. Ionically ($Ca^{2+}$) and covalently (e.g., ethylene diamine) crosslinked alginate foams and gels have been studied for use as tissue scaffolds (Kuo, C. K. and P. X. Ma, *Biomaterials*, 2001, 22(6):511-521; Suzuki, K. et al., *Neuroreport*, 1999, 10(14):2891-2894; Suzuki, Y. et al., *European Journal of Neuroscience*, 2000, 12:287-287). However, these materials have randomly oriented microstructures; therefore, a need exists for imposing structural order on growing/regenerating cells and tissues via scaffold architecture and geometry.

Alginate is a linear polysaccharide discovered by E.C.C. Stanford in 1880 obtained from alkali digestion of various brown sea algae (Schuberth, R. *Ionotropic Copper Alginates: Investigations into the formation of capillary gels and filtering properties of the primary membrane*, 1992, University of Regensburg: Regensburg; ISP Alginates, *Section 3: Algin-Manufacture and Structure*, in *Alginates: Products for Scientific Water Control*, 2000, International Specialty Products: San Diego, pp. 4-7). The polymer chain is composed of $\beta$-1$\rightarrow$4 linked D-mannuronic acid (M) and $\alpha$-1$\rightarrow$4 linked L-guluronic acid (G) monosaccharides found in three distinct blocks: polyM, polyMG and PolyG blocks. Compositional variation is a reflection of source and processing. The pKa's of the C5 epimers are 3.38 and 3.65 for M and G respectively with the pKa of an entire alginate molecule somewhere in-between (Schuberth, R. *Ionotropic Copper Alginates. Investigations into the formation of capillary gels and filtering properties of the primary membrane*, 1992, University of Regensburg: Regensburg; ISP Alginates, *Section 3: Algin-Manufacture and Structure*, in *Alginates: Products for Scientific Water Control*, 2000, International Specialty Products: San Diego, pp. 4-7).

Alginate forms colloidal gels (high water content gels, hydrogels) with divalent cations. In the alginate ion affinity series $Cd^{2+}>Ba^{2+}>Cu^{2+}>Ca^{2+}>Ni^{2+}>Co^{2+}>Mn^{2+}$, $Ca^{2+}$ is the best characterized and most used to form gels (Ouwerx, C. et al., *Polymer Gels and Networks*, 1998, 6(5):393-408). Studies indicate that Ca-alginate gels form via a cooperative binding of $Ca^{2+}$ ions by polyG blocks on adjacent polymer chains, the so-called "egg-box" model (ISP Alginates, *Section 3: Algin-Manufacture and Structure*, in *Alginates: Products for Scientific Water Control*, 2000, International Specialty Products: San Diego, pp. 4-7). G-rich alginates tend to form thermally stable, strong yet brittle Ca-gels that are likely to undergo syneresis, while M-rich alginates tend to form less thermally stable, weaker but more elastic gels.

Alginate is commercially used as a binding, stabilizing and/or thickening additive in many foods and cosmetics (ISP Alginates, *Section 3: Algin-Manufacture and Structure*, in *Alginates: Products for Scientific Water Control*, 2000, International Specialty Products: San Diego, pp. 4-7). Clinically, alginate is used in dental impression materials and hemostatic wound dressings (Blair, S. D. et al., *Brit. J. Surg.*, 1990, 77(5):568-570; Rives, J. M. et al., *Calcium alginate versus paraffin gauze in the treatment of scalp graft donor sites*, *Wounds-a Compendium of Clinical Research and Practice*, 1997, 9(6):199-205). Also, alginate-poly-L-lysine encapsulated pancreatic islet cells have been evaluated in a human clinical trial for treatment of type I diabetes (Soon-Shiong, P. *Adv. Drug Delivery Reviews*, 1999, 35(2-3):259-270; Sandford, P. A. and P. Spoonshiong, *Alginate Encapsulation-Up-* date on 1st Human Clinical-Trial with Encapsulated Human Islets in a Type-I-Diabetic Patient with Sustained Islet Function 16 Months Post Encapsulated Islet Transplant, Abstracts of Papers of the American Chemical Society, 1995, 209:44-CELL). Alginate-chitosan PEC beads and films have been made experimentally for cellular immunoprotective capsules and drug release devices (Yan, X. L. et al., *Chem. & Pharm. Bull.*, 2000, 48(7):941-946; Gaserod, O. et al., *Biomaterials*, 1999, 20(8):773-783; Bartkowiak, K and Hunkeler, D. *Annals of the New York Academy of Sciences*, 1999, 875:36-45). Ionically ($Ca^{2+}$) and covalently (e.g., ethylene diamine) crosslinked freeze-dried foams and gels have been studied for use as tissue scaffolds (Kuo, C. K. and P. X. Ma *Biomaterials*, 2001, 22(6):511-521; Suzuki, K. et al., *Neuroreport*, 1999, 10(14):2891-2894; Suzuki, Y. et al., *Euro. J. Neurosci.*, 2000, 12:287-287).

Copper capillary alginate gels (CCAG) have been known in the literature for at least 40 years (Schuberth, R., *Ionotropic Copper Alginates: Investigations into the formation of capillary gels and filtering properties of the primary membrane.* 1992; Thiele, H., *Histolyse und Histogenese, Gewebe und ionotrope Gele, Prinzip einer Stukturbildung.* 1967). The gels are essentially formed by allowing solutions of $Cu^{2+}$ to diffuse uniformly into viscous solutions of alginate. During this diffusion process, it is reported that fluid instabilities arise from the friction forces involved in the contraction of alginate polymer chains to the newly forming gel front (Thumbs, J. and H. H. Kohler, *Chemical Physics*, 1996, 208(1):9-24). Convecting tori, similar to those observed in the Raleigh-Benard model of heat convection, result from these hydrodynamic instabilities. In a sense, these tori tunnels parallel capillaries through the forming gel in the direction of diffusion. A continuous, tubular microstructure is mapped onto the forming gel due to the convective-like process the system undergoes to dissipate energy. Gel capillary diameter can be adjusted by manipulating singly, or in combination, the initial alginate concentration, initial $Cu^{2+}$ concentration or system pH (Schuberth, R., *Ionotropic Copper Alginates: Investigations into the formation of capillary gels and filtering properties of the primary membrane.* 1992; Thumbs, J. and H. H. Kohler, *Chemical Physics*, 1996, 208(1):9-24; Thiele, H., *Histolyse und Histogenese, Gewebe und ionotrope Gele, Prinzip einer Stukturbildung.* 1967).

However, in common tissue culture media, CCAG alone swells, loses mechanical properties, and eventually dissolve due to a loss of copper ions that are released into the surrounding fluid environment. Accordingly, there is a need for a modified CCAG that provides a stable tissue scaffold in a cell culture environment or within a human or animal.

BRIEF SUMMARY OF THE INVENTION

It is an object of the present invention to prepare an advanced biomaterial scaffold possessing regular, continuous microtubular architectures. It is a further object of the present invention to synthesize artificial peripheral nerve conduits constructed from modified copper capillary alginate gels.

The present invention provides methods of preparing stabilized copper capillary alginate gels and compositions comprising the stabilized gels. Advantageously, the stabilized gels of the present invention can be used in vitro or in vivo for the growth of healthy cells without being toxic to cells or surrounding environment.

The gels are preferably stabilized via ion exchange with barium, or by the formation of a polyelectrolyte laminate with an appropriate electrostatically charged molecule, for example, chitosan, its derivatives, oligochitosan, and polylysine, or both. The gels may optionally be stabilized by cross-linking with a carbodiimide or a divalent salt, provided the resulting stabilized gel provides a healthy, physiological environment for growing cells or for implanting into human or non-human animals. The stabilized gels possess a regular capillary microstructure running the entire length of the gel, and the capillary diameter can be adjusted between about 3 µm to about 300 µm (Thiele, H., *Histolyse und Histogenese, Gewebe und ionotrope Gele, Prinzip einer Stukturbildung.* 1967). Preferably, the diameter is within the range of about 10 µm to about 250 µm. More preferably, the diameter is within the range of about 25 µm to about 30 µm. The stabilized gel's structure, positive surface charge and hydrophilic character make for scaffolds with excellent properties conducive to growth and regeneration of multiple cell types.

The present invention also provides methods for promoting the growth of cells and tissues within a human or animal patient.

Additionally, the present invention also provides methods for controlling stem cell proliferation and/or differentiation.

BRIEF DESCRIPTION OF THE FIGURES

FIG. 6 shows a SEM image viewing capillaries of a raw CCAG sample end-on.

FIG. 9A shows the phase contrast image. FIG. 9B shows the GFP filter. FIG. 9C shows a nuclear staining with Hoechist. FIG. 9D shows a confocal microscopic image. The bar at the lower right corner is 50 µm long.

FIG. 14A is a barium stabilized CCAG optical micrograph showing brown precipitate. FIG. 14B is a barium stabilized CCAG optical micrograph showing shimmering precipitate. Scale bar=100 µm.

FIGS. 15A-15G show a summary of barium stabilized CCAG SEM/EDS and X-ray mapping data. FIG. 15A is a secondary electron image. FIG. 15B is a backscatter electron image. FIG. 15C is a representative EDS spectrum. FIGS. 15D-15G are an X-ray map group. Scale bars=50 µm.

FIG. 16A is a 4000× SEI image. FIG. 16B is a complementary BSE image to FIG. 16A (note the charge wave distortion in the central region of this micrograph). FIG. 16C is a 15000× SEI image of copper-rich nanoparticle formations. FIG. 16D is a small combination false color image of X-ray map group. FIGS. 16E-16H are an X-ray map group. Scale bar for 16C=2 μm; all others=5 μm.

FIG. 17A is a secondary electron image. FIG. 17B is a backscatter electron image. FIG. 17C is a representative EDS spectrum. FIGS. 17D-17G are an X-ray map group. Scale bars=50 μm.

FIG. 21A is a day 0 phase contrast image. FIG. 21B is a complementary day 0 GFP-filtered image. FIG. 21C is a day 6 phase contrast image. FIG. 21D is a complementary day 6 GFP-filtered image. FIG. 21E is a day 9 phase contrast image. FIG. 21F is a complementary day 9 GFP-filtered image. Scale bar=100 μm for all images.

FIG. 24A: Day 0D; FIG. 24B: Day 0M/D; FIG. 24C: Day 0M; FIG. 24D: Day 2D; FIG. 24E: Day 2M/D; FIG. 24F: Day 2M; FIG. 24G: Day 4D; FIG. 24H: Day 4M/D; FIG. 24I: Day 4M. Scale bar=100 μm for all images.

DETAILED DESCRIPTION OF THE INVENTION

The present invention is directed to copper capillary alginate gels (CCAG) stabilized in a fluid and biological environment and their methods of preparation and use. In one embodiment, the CCAG are stabilized with cross-linking to at least one carbodiimide. In a preferred embodiment, stabilization involves exchanging ions with a cation, preferably barium, forming a polyelectrolyte laminate complex (PEC) by adding chitosan, or oligochitosan, or a combination of both.

The gels of the present invention are useful as biomaterial scaffolds to provide a structure useful for containing, growing, and/or regenerating biological agents for subsequent in vivo implantation in humans or animals. One aspect of the present invention is directed to a modified or stabilized CCAG, which is useful as a biomaterial scaffold. CCAG comprises a soft hydrogel having a continuous parallel microtubular architecture. Beneficially, the stabilized CCAG can impose structural order on growing and regenerating cells and tissues. The microtubular or capillary diameter can range from about 3 μm to about 300 μm. Preferably, the capillary diameter is within the range of about 10 μm to about 250 μm. More preferably, the capillary diameter is within about 25 μm to about 30 μm.

Advantageously, the cell morphology can be designed to promote efficient cell growth. The skilled artisan would understand that cells behave differently at different curved surfaces. For example, the cells might propogate differently. Morphology can be adjusted to the desired shape via freeze drying techniques.

Figure 13:
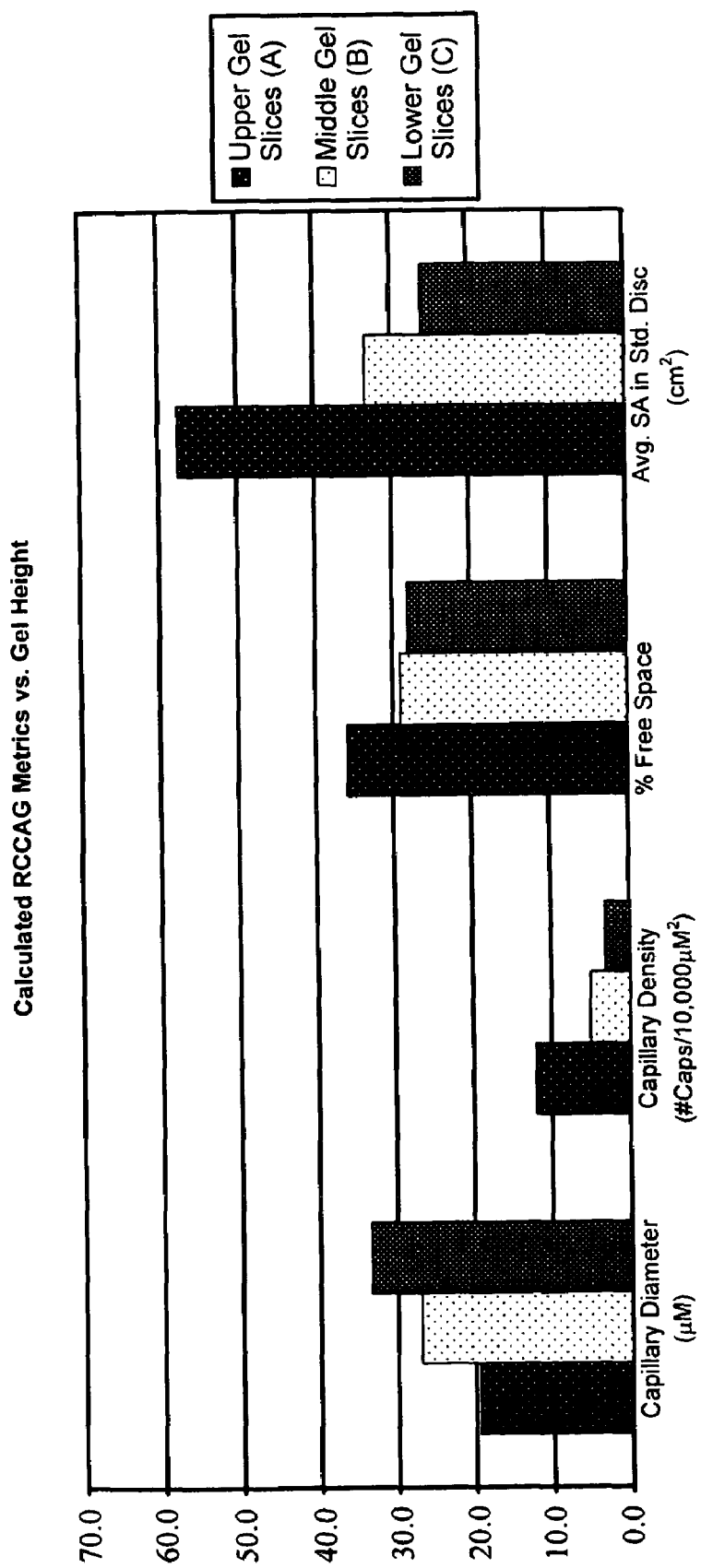
FIG. 13 is a graph of calculated RCCAG metrics vs. Parent Gel Section Level.

Capillary diameter can vary at different gel levels because it is a function of gel thickness. Other physical properties of the subject scaffolds also vary with gel thickness. For example, capillary density decreases as parent gel thickness increases, wherein a parent gel refers to the initially grown raw CCAG from which samples are derived to make stabilized scaffolds. The average surface area also decreases as parent gel thickness increases (FIG. 13).

Advantageously, a stabilized CCAG of the present invention possesses superior properties over a CCAG alone when utilized in a fluid environment. The stabilized CCAG experiences a decrease in swelling and greater maintenance of mechanical properties. The stabilized gel's structure, positive surface charge and hydrophilic character are useful for preparing scaffolds for growth and regeneration of multiple cell types. The stabilizing agent can be selected from a variety of compounds and ions. The key is for the stabilizing agent to be non-toxic to a growing cell or its surrounding environment or to be bound to the alginate gel in such a way that it will not be released into the surrounding physiological environment. Examples can include, without limitation, cations, polysaccharides and carbodiimides. Preferably, the cations are divalent cations. More preferably, the divalent cation is a barium ion. Barium ion is an example of an agent that is toxic to cells. However, it remains bound to the alginate gel in physiological environment, thus negating its toxicity. Preferably, the polysaccharide is chitosan or oligochitosan. Preferably, the carbodiimide is selected from N-ethyl-N'-(3-dimethylaminopropyl)-carbodiimide, NN'-dicyclohexyl-carbodiimide (DCC), N'-diisopropyl-carbodiimide, N'N'-di-tert-butylcarbodiimide 1-cyclo-hexyl-3-(4-diethylaminocyclohexyl)carbodiimide, 1,3-di-(4-diethylaminocyclo-hexyl)carbodiimide, 1-cyclohexyl-3-(-diethylaminoethylcarbodiimide, and 1-cyclohexyl-1-cyclohexyl-3-(2-morphonlinyl-(4)-ethyl) carbodiimide 1-cyclohexyl-3-(4-diethyl-aminocyclohexyl) carbodiimide. Also, because the scaffolds comprise potentially edible components, they are useful as the basis for synthetic meat products that grow and regenerate animal cells. In contrast, the CCAG alone dissolves in cell culture environments, and copper ions leach out and infiltrate the surrounding environment. Thus, one specific embodiment of the present invention is directed to a biomaterial scaffold, which is non-toxic to a cell in vivo or in vitro, wherein the scaffold comprises an alginate gel and at least one stabilizing agent; wherein the gel further comprises a plurality of continuous microtubular copper capillaries.

The compositions (e.g., stabilized gel scaffolds) of the present invention can be used as a vehicle for the in situ delivery of biologically active agents. The biologically active agents incorporated into, or included as an additive within, the composition of the present invention can include, without limitation, medicaments, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composition into a patient and to promote subsequent integration and healing processes. The active agents include, but are not limited to, antibodies, antibody fragments, antibiotics, antifungal agents, antibacterial agents, anti-viral agents, anti-parasitic agents, growth factors, neurotrophic factors, angiogenic factors, anaesthetics, mucopolysaccharides, metals, cells, proteins, polynucleotides, polypeptides enzymes, degradation agents, lipids, carbohydrates, chemical compounds such as pharmaceuticals and other wound healing agents. The substances can be therapeutic agents, diagnostic materials, and/or research reagents.

Examples of proteins that may be incorporated into or otherwise associated with the composition are collagen (of the various types) and fibronectin. The composition can be adapted to allow delayed release of the biologically active agents, or controlled release over time.

After processing the compositions of the present invention, live cells can be subsequently allowed to infiltrate the composition through tissue engineering techniques. Advantageously, the parallel microtubular architecture of the scaffold (e.g., conduit) of the invention facilitates tissue ingrowth and may be infiltrated with nutrient and/or cellular material at the implant site or in cell cultures. Nutrients may also diffuse across the stabilized CCAG to nourish cells seeded within the copper capillaries.

As indicated above, cells can be seeded onto and/or within the copper capillaries of the alginate gels of the present invention. Likewise, tissues such as cartilage or nerve tissue can be associated with the gels prior to implantation within a patient. The cells utilized may include those cells arising from the ectoderm, mesoderm, or endoderm germ cell layers. Examples of cells include, but are not limited to, pancreatic islet cells, bone cells (such as osteoclasts, osteoblasts, chondrocytes, and osteocytes), blood cells, marrow cells, epithelial cells, neural cells (e.g., neurons, astrocytes, and oligodendrocytes), muscle cells, adipocytes, tendon cells, ligament cells, dermal cells, fibroblasts, and dental cells (odontoblasts and ameloblasts). Seeded cells can be autogenic, allogenic, or xenogenic to the patient in which the scaffold is implanted. Seeded cells can be encapsulated or non-encapsulated. The cells can be stem cells or progenitor cells (such as stem cells or progenitor cells of any of the aforementioned differentiated cell types), or mature, differentiated cells. For example, the cells seeded onto and/or within the alginate gels can be hematopoietic stem cells, mesenchymal stem cells, neural stem cells, or others. The stem cells, progenitor cells, or mature cells can be genetically modified or non-genetically modified. As used herein, the term "cell" is intended to include primary cells, cells of cell culture, and cells of cell lines (e.g., cells of tumors or immortalized cells), unless otherwise specified. As will be understood by one of skill in the art, there are over 200 cell types in the human body. The methods and compositions of the present invention may utilize any of these cell types, singly or in combination. Other cells suitable for use with the compositions and methods of the present invention include those disclosed by Spier R. E. et al., eds., *The Encyclopedia of Cell Technology* (2000), John Wiley & Sons, Inc., and Alberts B. et al., eds., *Molecular Biology of the Cell* (1994), $3^{rd}$ ed., Garland Publishing, Inc., e.g., pages 1188-1189, which are incorporated herein by reference in their entireties.

In yet another embodiment, the scaffolds of the present invention can be used as implants to repair bone defects. The scaffolds can comprise components such as particles or bioglass, which impart a rigid structure to the scaffold.

One embodiment of the present invention is a negatively charged CCAG scaffold. Preferably, barium ions stabilize the CCAG by additional cross-linking with the alginate within and throughout the scaffold, although other ions may be used, for example, $Cd^{2+}$, $Cu^{2+}$, $Ca^{2+}$, $Ni^{2+}$, $Co^{2+}$, and $Mn^{2+}$. Advantageously, the pore morphology of the barium-stabilized scaffold is round when placed in fluid environment. FIGS. 14A, 14B, 15A-15G, and 16A-16H all show various images of barium stabilized CCAG produced according to the methods of the subject invention.

Another embodiment of the invention is a positively charged CCAG scaffold. In another specific embodiment, oligochitosan is used to stabilize the CCAG. The oligochitosan and alginate gel react to form a cross-linked skin surrounding an inner core of CCAG. FIGS. 17A-17G and 18 depict various properties of the oligochitosan stabilized CCAG produced according to the methods of the present invention.

In yet another embodiment, both an ion exchange with cations like barium and a reaction with at least one electrostatic moiety, which form a polyelectrolyte complex (PEC), are utilized in stabilizing the CCAG scaffold. These moieties can include, without limitation, chitosan, its derivatives, oligochitosan, poly-lysine, carbodiimides, and ethylene diamine. Other cations, for example, $Cd^{2+}$, $Cu^{2+}$, $Ca^{2+}$, $Ni^{2+}$, $Co^{2+}$, and $Mn^{2+}$, may also be used. Advantageously, cells adhere, spread and proliferate on positively charged chitosan surfaces. Also, the PEC stabilized scaffolds can be prepared with multiple PEC layers. Preferably, there are three to five layers of PEC. The advantages of multiple layered CCAG are increased mechanical integrity and, if used as a carrier for drugs, greater flexibility in controlling diffusion rates.

Figure 1:
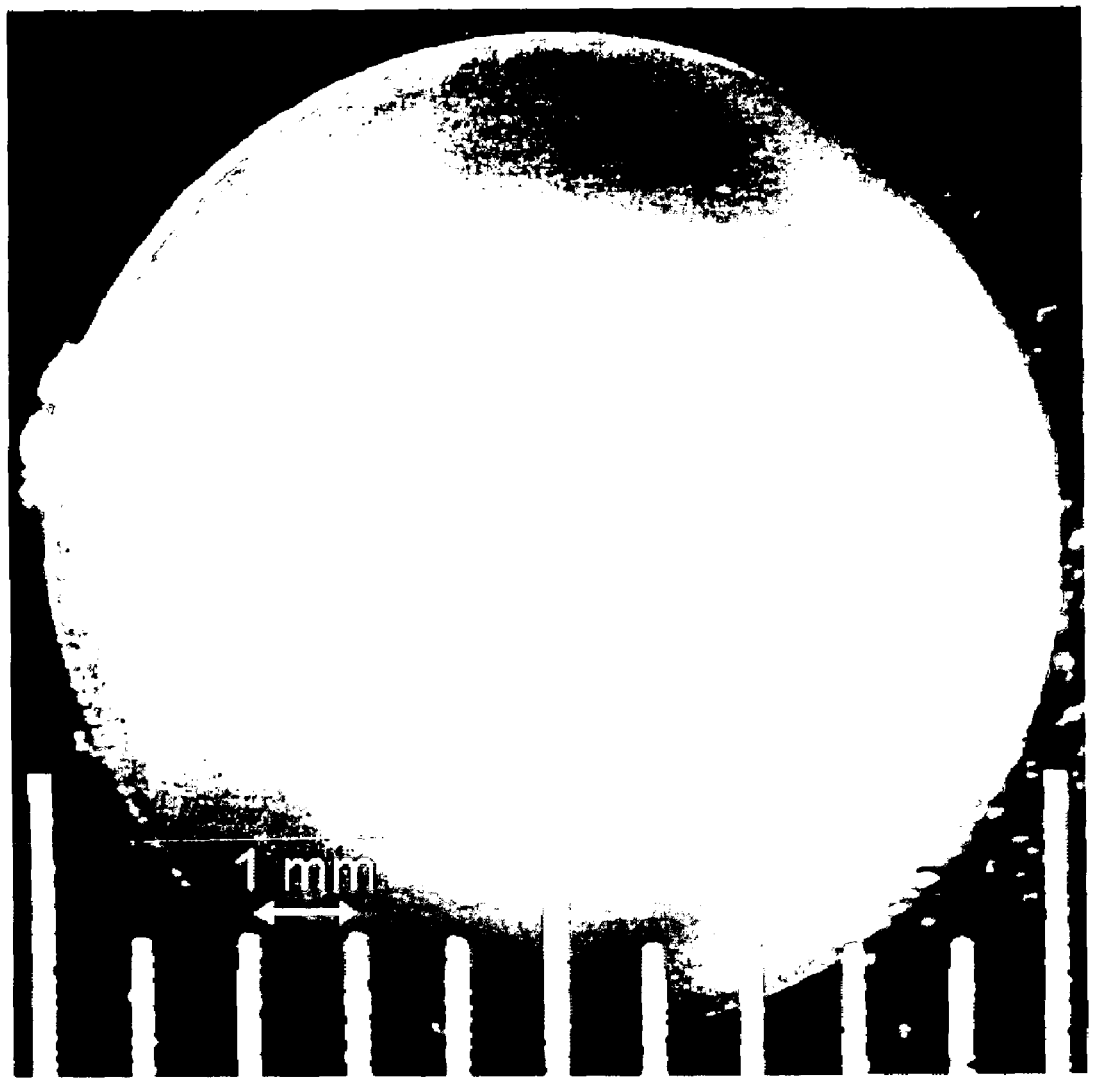
FIG. 1 shows a top-down view of the low magnification optical micrograph of a raw CCAG sample. The sample plane is perpendicular to the long capillary axis.
Figure 2:
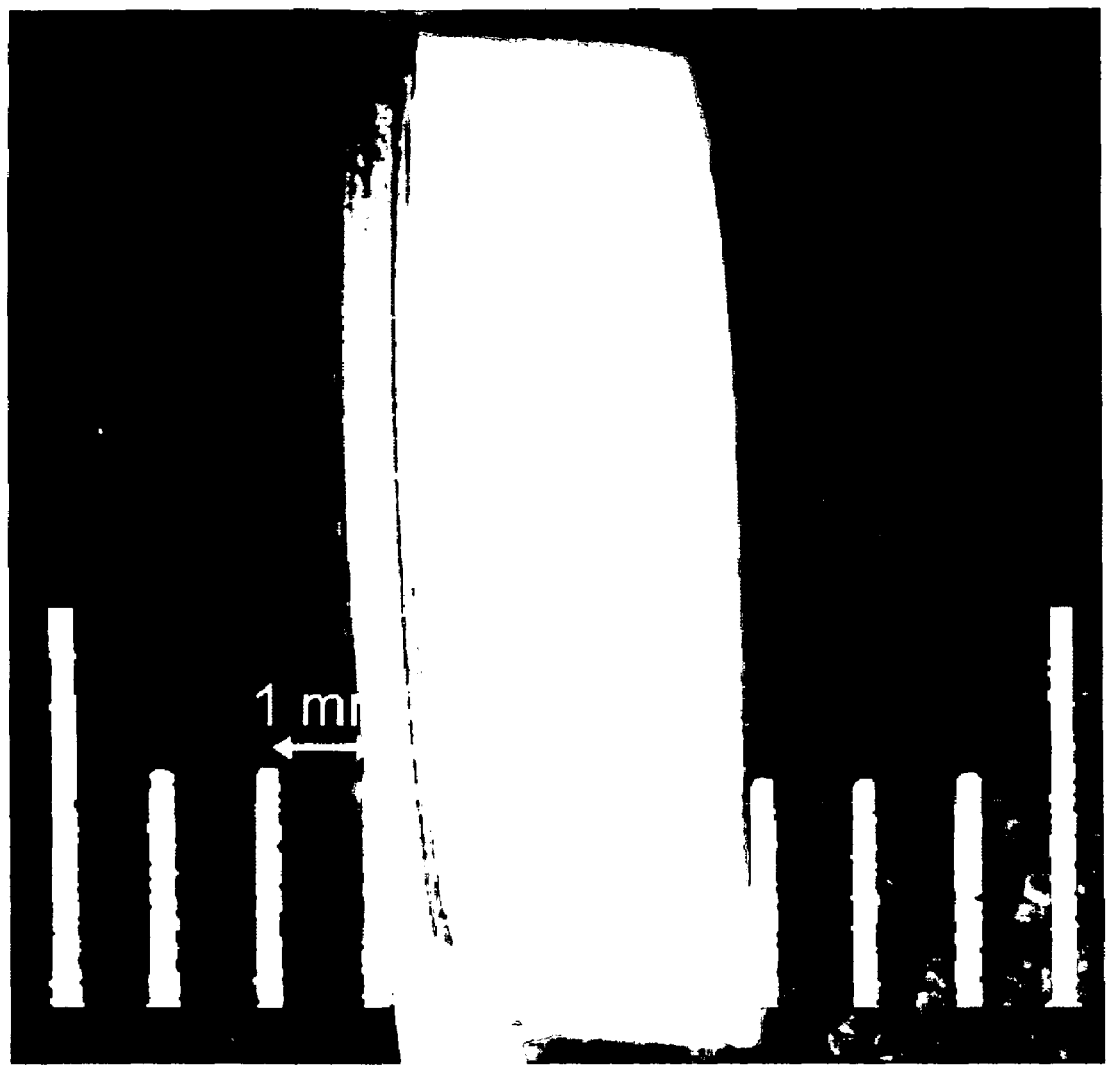
FIG. 2 shows a side view of the low magnification optical micrograph of a typical raw CCAG sample. The sample plan contains the capillary long axis.
Figure 3:
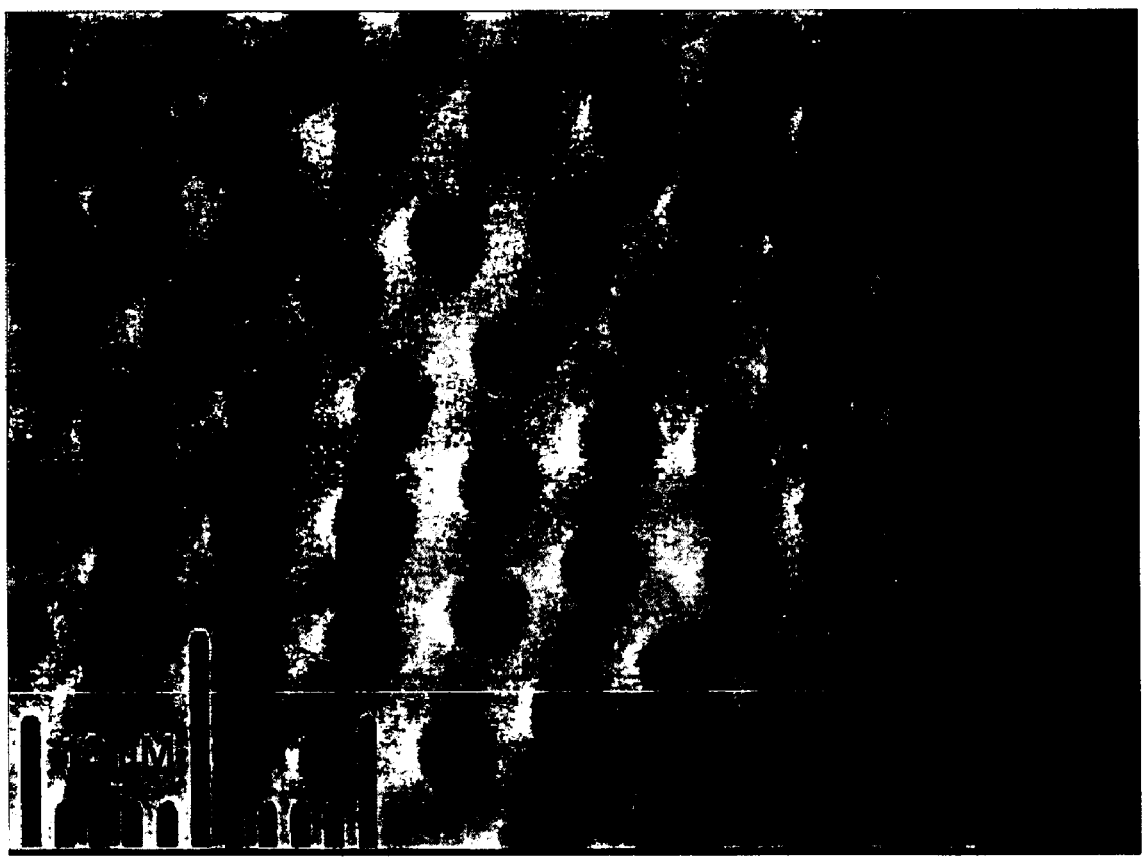
FIG. 3 shows an optical micrograph of a typical raw CCAG sample, which illustrates the gel capillary architecture.
Figure 4:
FIG. 4 shows an optical micrograph of chitosan-stabilized CCAG created with a syringe pump-flowcell. The morphology of the capillaries changed from circular to non-circular after the $Cu^{2+}$ ions were removed.
Figure 5:
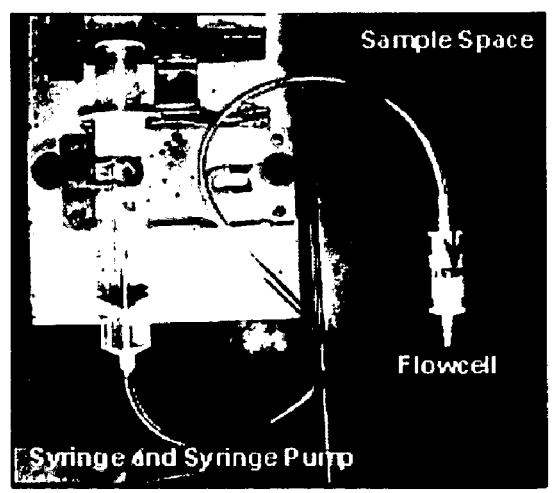
FIG. 5 shows the flow cell set up utilized in Examples 2 and 3 to prepare chitosan stabilized CCAG.

Methods of preparing of CCAG are well known in the art, for example, as disclosed by Hassan et al., *Journal of Polymer Science*, 1991, 29(11):1645; *European Polymer Journal*, 1988, 24(12):1173; Thiele, H. *Histolyse und Histogenese, Gewebe und ionotrope Gele, Prinzip einer Stukturbildung*, 1967, Frankfurt: Akademische Verlagsgesellschaft; Schuberth, R. *Ionotropic Copper Alginates: Investigations into the formation of capillary gels and filtering properties of the primary membrane*, 1992, University of Regensburg: Regensburg. FIGS. 3, 4, and 5 show raw CCAG samples prior to stabilization according to the methods of the present invention.

The base alginate may be derived from brown sea algae. The alginate can be derived from, for example and without limitation, *Laminaria hyperborea* or *Macrocystis pyrifera*.

The method of preparing a barium stabilized copper capillary gel comprises initially washing CCAG in deionized (DI) water for a sufficient period of time to remove excess, unreacted copper ions, submerging CCAG in a aqueous barium solution while agitating, and washing the resulting scaffold. Preferably, the barium solution is $Ba(OH)_2$. The concentration of the $Ba(OH)_2$ solution varies from about 0.01 M to about 0.1 M and is preferably about 0.05M $Ba(OH)_2$. The submerging step lasts for a period of time sufficient for the $Ba^{2+}$ ions to diffuse across the CCAG. The diffusion is measurable by observing the gel color change from a light blue-green to a deep blue. Preferably, the submerging step takes place within about 12 to about 48 hours. More preferably, the submerging step takes place within about 12 to about 24 hours. Optionally, the barium solution can be completely exchanged at periodic intervals. Preferably, a fresh solution of about 0.05M $Ba(OH)_2$ is exchanged with the spent solution about every twelve hours. The final washing step occurs in a DI water bath, a physiologically balanced salt solution wash, or both. These steps are conducted at temperatures that vary between about 13° C. and about 33° C. Preferably, the steps take place at room temperature (around 23° C.). Poorly washed samples have exhibited black layers within the gel.

The present invention also provides chitosan-stabilized CCAG and methods for their preparation. Chitosan is a natural polysaccharide prepared from crustacean cells, which is known to possess many beneficial properties, such as biocompatibility, wound-healing properties, and anti-microbial properties (Otterlei, M. et al. *Vaccine,* 1994, 12:825-32; Muzzarelli, R. et al. *Biomaterials,* 1988, 10:598-603; Pappineau, A. M. et al. *Food Biotechnol,* 1991, 5:45-47; Erbacher, P. et al. *Pharm Res,* 1998, 15:1332-9; Richardson, S. C. et al. *Int J Pharm,* 1999, 178:231-43). Oligochitosan is a small chained, thus a low molecular weight, chitosan. Advantageously, oligochitosan is water soluble at a neutral pH.

One method of preparing a chitosan-stabilized CCAG comprises, washing the CCAG in a DI water bath to remove any excess copper ions, contacting a chitosan solution with the CCAG by flowing the solution through the microtubular structure through the CCAG, and washing the resulting stabilized scaffold in a solution to remove any unbonded or excess chitosan. One washing step can be omitted. The concentration of the chitosan solution can vary between about 0.1 w/v % and about 3 w/v %. Preferably, the concentration of the chitosan solution is about 0.2% w/v to about 2% w/v. More preferably, the concentration of the solution is about 2% w/v. Advantageously, the solvent of the solution can be water or acetic acid.

Optionally, the contacting and second washing steps can be repeated alternating alginate and chitosan or oligochitosan solutions to produce multi-layers of PEC on the scaffold. Preferably, the contacting and second washing steps are repeated about three to five times to produce three to five layered CCAG.

One method of preparing a CCAG scaffold stabilized by both barium and chitosan involves washing raw CCAG in DI water for a sufficient period of time to remove excess, unreacted copper ions, submerging CCAG in an aqueous barium solution while agitating, washing the resulting scaffold, contacting a chitosan solution with the barium-stabilized CCAG, and a third washing to remove any unbound or excess chitosan. Again, one or two of the washing steps may be omitted.

The present invention also provides methods for promoting the growth of cells and tissues within a patient by implanting a stabilized gel scaffold of the present invention within the patient. The gels of the present invention provide ideal conditions for cell growth in scaffolds because it is hydrophilic, its surface is positively charged, and it has an inherently strong structure.

According to a method of the present invention, a therapeutically effective amount of the stabilized gel can be implanted, applied, or otherwise administered at a target site. The amount to be administered will depend upon the particular medical application, and the clinical outcome that is sought. According to the method of the present invention, the composition can be applied so that it directly contacts existing tissue adjacent to, or defining, the site of a defect or discontinuity, or the composition can be contacting another implant, or both.

The scaffolds of the present invention may be any shape suitable for the particular in vitro or in vivo application. Where the scaffold is a conduit, for example, the conduit preferably has at least two openings and a passageway connecting the openings. The exterior of the conduit may possess any shape suitable for the application. For example, the exterior of the conduit may be tubular in shape. The wall of the passageway of the conduit (i.e., the interior) also may possess any shape suitable for the application. The preferred shape can be produced utilizing freeze-drying techniques, as noted above. Thus, cross-sections taken at different locations along the length of the conduit may have differing areas, revealing an irregularly-shaped interior. In one embodiment, the cross-sections may be round, elliptical, or irregularly polygonal, depending on the application. Scaffolds of the present invention may be used for bone, cartilage, and/or soft tissue repair. Scaffolds of the present invention may be used in virtually all instances when it is desirable to provide a substrate for the growth of cells onto or into a tissue replaceable matrix, either in vitro or in vivo. The scaffold itself may be molded or cut into a specific shape that is applicable for its end usage.

The disclosed methods and compositions can be utilized in a variety of different clinical settings. In the case of promoting repair of a nerve pathology, for example, the scaffold of the present invention is preferably in the form of a conduit for repairing any nerve gaps or discontinuity in the fascicular layers, such that the conduit is capable of supporting and/or holding permissive tissues. Such nerve pathologies may arise from a wide variety of problems, including mechanical, thermal, or electrical trauma, congenital defects, or acquired disease states.

Traditional nerve grafts involve harvesting donor nerves and placing them within a defect to bridge a nerve gap. The "nerve cables" as they are called, are secured between or within these nerve defects using microsurgical techniques and very small (e.g., 9-0 or 10-0) nylon sutures. A similar approach can be employed according to the present invention wherein conduits are placed much like the nerve cables.

As indicated above, optionally, the compositions of the present invention can be used as a carrier for the in situ delivery of biological agents, thus providing a method for delivering such biologically active agents to a patient in need thereof (e.g., as a drug delivery mechanism).

The compositions of the present invention can also be used as implants at the site of bone defect or injury, thus providing methods for repairing the orthopedic defect.

Another aspect of the present invention pertains to providing methods for utilizing the biomaterial scaffolds as platforms for growing stem cells and for controlling any differentiation. Advantageously, the unique architecture of the present invention's biomaterials scaffolds provides an environment wherein stem cells can be cultivated in an undifferentiated state for extended periods or indefinitely in vitro. Specifically, the continuous parallel microtubular capillaries of the subject scaffolds are ideal for seeding with stem cells. The narrow diameter of the individual capillaries force each of the individual seeded stem cells to line up and within the capillary structure. Advantageously, the hydrogel consistency of the stabilized alginate scaffold permits nutrient and oxygen diffusion from the culture medium to the seeded cells.

In a specific embodiment, murine embryonic stem cells (MES) are seeded in oligochitosan CCAG. mES cells were maintained in an undifferentiated state on gelatin-coated dishes in Knock-out DMEM (GIBCO BRL, Grand Island, N.Y.) containing 10% knockout serum replacement (GIBCO BRL), 1% fetal bovine serum (Atlanta biologicals, Norcross, Ga.), 2 mM L-glutamine, 100 units/ml penicillin, 100 µg/ml streptomycin, 25 mM HEPES (GIBCO BRL), 300 µM monothioglycerol (Sigma, St. Louis, Mo.), and 1000 unit/ml recombinant mouse LIF (ESGRO) (Chemicon, Temecula, Calif.). To seed mES cells into OCCAG, the medium was discarded and washed once with 5 ml of phosphate buffered saline (PBS/pH7.5). 0.5 ml of Trypsin/EDTA was added and allowed to sit for 2-3 minutes at room temperature. The flask was tapped to remove the cells. 5 ml of serum containing medium and pipetting was added. The cells were spun down and resuspended in the medium IMDM containing 2 mM L-glutamine, 100 units/ml penicillin, 100 µg/ml streptomycin (GIBCO BRL), 20% fetal bovine serum (Atlanta biologicals), and 300 µM monothioglycerol (Sigma) to make $1\times10^6$/ml cell suspension. The cell suspension was applied to one end of the OCCAG capillaries and suction was applied to the other end of the capillaries until the cells filled the scaffold. Both ends of the scaffold was sealed by 10% agar/PBS, and the medium was changed every other day.

Advantageously, stem cells survive and proliferate in the present invention's CCAG. Moreover, seeding the ES cells in the capillaries, block aggregation-induced primitive endoderm specification. Thus, the biomaterial scaffolds of the present invention are useful as tools to direct stem cell differentiation to other lineages. Embryonic stem cells can be directly differentiated into, for example, an early mesoderm phenotype.

Without being limited by theory, the biomaterial scaffolds may influence ES cell lineage commitment in a variety of their advantageous features. First, the capillary diameter prevents cell aggregation, thereby preventing differentiation into primitive endoderm. Second, the capillary cross-sections may be adjusted to obtain different curves along the inner surface of the capillaries. The skilled artisan would understand that cells propogate differently in response to different shaped capillaries. Furthermore, the inner surface can be modified with chemicals or natural extracellular matrices. The type of features all contribute to the physical stress placed on cells. Alone or in combination, controlling these aspects of the biomaterial scaffolds direct lineage commitment.

Additionally, the cell culture medium can be adjusted by adding growth factors, cytokines, drugs, or other small molecules as directed below.

Figure 12:
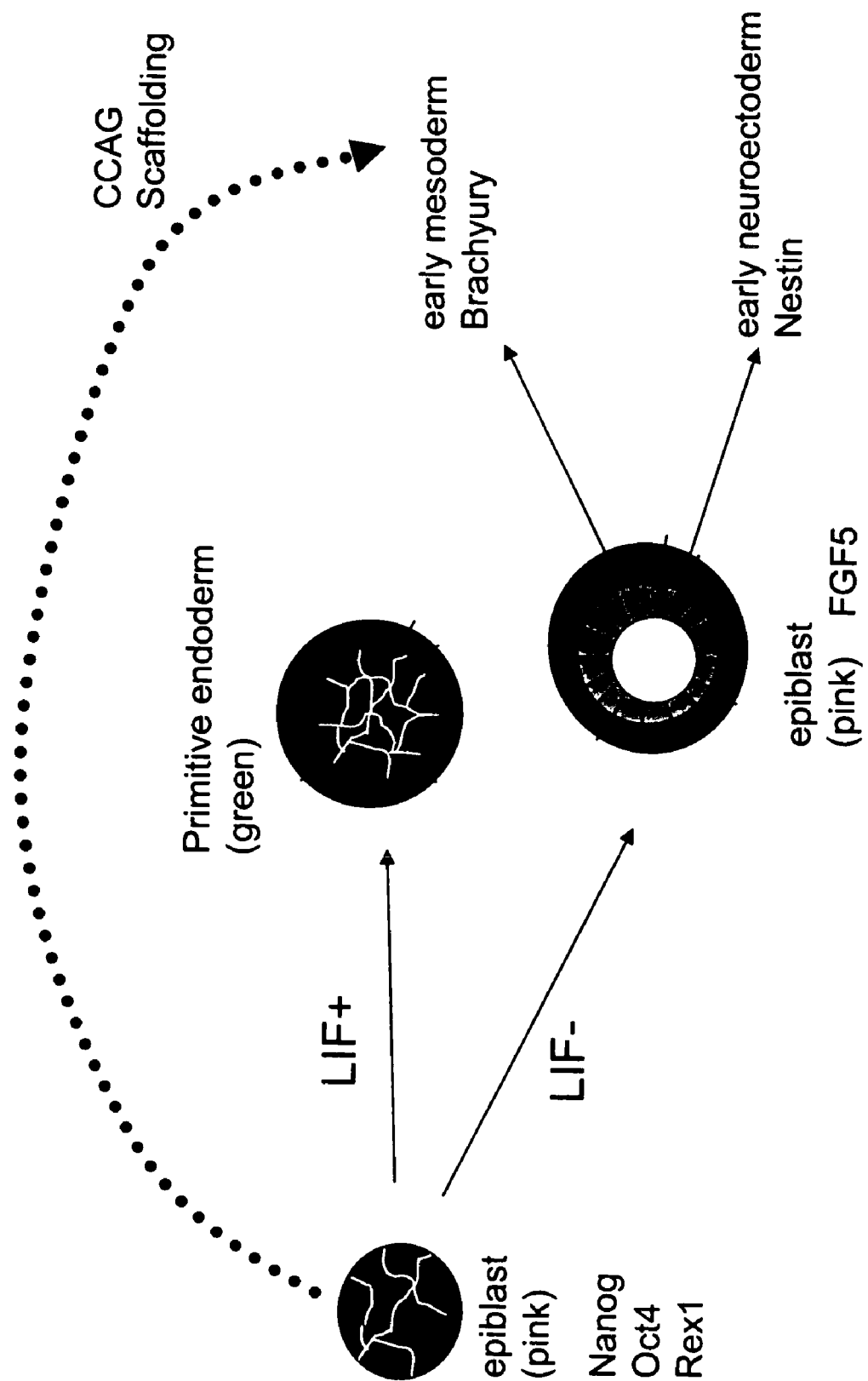
FIG. 12 shows a schematic diagram of initial cell fate specification from ES cells in vitro.

FIG. 12 illustrates various routes to control stem cell fate.

Preferably, leukemia inhibitory factor (LIF) is utilized to cultivate the cells. However, a variety of culture media can be utilized to culture the stem cells according to the methods of the present invention. For example, if low calcium conditions are desired, Minimum Essential Medium (MEM), Joklik modification for suspension culture, with L-Glutamine, without calcium chloride and sodium bicarbonate (SIGMA, St. Louis, Mo.; Product No. M0518), or other low calcium media can be used (Eagle, H. et al., *J. Biol. Chem.*, 214:845-847, 1956; Eagle, H., Media for Animal Cell Culture, Tissue Culture Association Manual, 3:517-520, 1976; Eagle, H., *Science*, 130:432-437, 1959; Eagle, H., *Science*, 122:501, 1955).

Cells can be stimulated to differentiate by contact with one or more differentiation agents (e.g., trophic factors, hormonal supplements), such as forskolin, retinoic acid, putrescin-transferrin, cholera toxin, insulin-like growth factor (IGF), transforming growth factor (e.g., TGF-α, TGF-β), tumor necrosis factor (TNF), fibroblast growth factor (FGF), epidermal growth factor (EGF), granulocyte macrophage-colony stimulating factor (GM-CSF), hepatocyte growth factor (HGF), hedgehog, vascular endothelial growth factor (VEGF), thyrotropin releasing hormone (TRH), platelet derived growth factor (PDGF), sodium butyrate, butyric acid, cyclic adenosine monophosphate (cAMP), cAMP derivatives (e.g., dibutyryl cAMP, 8-bromo-cAMP), phosphodiesterase inhibitors, adenylate cyclase activators, prostaglandins, ciliary neurotrophic factor (CNTF), brain-derived neurotrophic factor (BDNF), neurotrophin 3, neurotrophin 4, interleukins (e.g., IL-4), interferons (e.g., interferon-gamma), potassium, amphiregulin, dexamethasone (glucocorticoid hormone), isobutyl 3-methyulxanthine, somatostatin, lithium, and growth hormone.

The term "chitosan", as used herein, will be understood by those skilled in the art to include all derivatives of chitin, or poly-N-aceryl-D-glucosamine (including all polyglucosamine and oligomers of glucosamine materials of different molecular weights), in which the greater proportion of the N-acetyl groups have been removed through hydrolysis. Generally, chitosans are a family of cationic, binary hetero-polysaccharides composed of (1→4)-linked 2-acetamido-2-deoxy-β-D-glucose (GlcNAc, A-unit) and 2-amino-2-deoxy-β-D-glucose, (GlcN; D-unit) (Varum K. M. et al., *Carbohydr. Res.*, 1991, 217:19-27; Sannan T. et al., *Macromol. Chem.*, 1776, 177:3589-3600). Preferably, the chitosan has a positive charge. Chitosan, chitosan derivatives or salts (e.g., nitrate, phosphate, sulphate, hydrochloride, glutamate, lactate or acetate salts) of chitosan may be used and are included within the meaning of the term "chitosin". As used herein, the term "chitosan derivatives" are intended to include ester, ether or other derivatives formed by bonding of acyl and/or alkyl groups with OH groups, but not the $NH_2$ groups, of chitosan. Examples are O-alkyl ethers of chitosan and O-acyl esters of chitosan. Modified chitosans, particularly those conjugated to polyethylene glycol, are included in this definition. Low and medium viscosity chitosans (for example CL113, G210 and CL110) may be obtained from various sources, including PRONOVA Biopolymer, Ltd. (UK); SEIGAGAKU America Inc. (Maryland, USA); MERON (India) Pvt, Ltd. (India); VANSON Ltd. (Virginia, USA); and AMS Biotechnology Ltd. (UK). Suitable derivatives include those which are disclosed in Roberts, Chitin Chemistry, MacMillan Press Ltd., London (1992). Optimization of structural variables such as the charge density and molecular weight of the chitosan for efficiency of delivery of biologically active agents is contemplated and encompassed by the present invention.

The chitosan (or chitosan derivative or salt) preferably used has a molecular weight of 1,000 Dalton or more, preferably in the range 1,000 to 4,000 Dalton. Chitosans of different low molecular weights can be prepared by enzymatic degradation of chitosan using chitosanase or by the addition of nitrous acid. Both procedures are well known to those skilled in the art and are described in various publications (Li et al., *Plant Physiol. Biochem.*, 1995, 33:599-603; Allan and Peyron, *Carbohydrate Research*, 1995, 277:257-272; Damard and Cartier, *Int. J. Biol. Macromol.*, 1989, 11:297-302). Preferably, the chitosan is water-soluble and may be produced from chitin by deacetylation to a degree of greater than 40%, preferably between 50% and 98%, and more preferably between 70% and 90%.

As used in this specification and the appended claims, the singular forms "a", "an", and "the" include plural reference unless the context clearly dictates otherwise. Thus, for example, a reference to "a scaffold" includes more than one such scaffold, a reference to "a capillary" includes more than one such capillary, a reference to "a biological or biologically active agent" includes more than one such agent, a reference to "a cell" includes more than one such cell, and the like.

As used herein, the terms "administer", "apply", "transplant", "implant", "deliver", or grammatical variations thereof, are used interchangeably and intended to include all methods known in the art for delivery of cells to a patient. For example, cells cultured according to the methods of the subject invention can be administered locally (e.g., to one or more target anatomical sites), systemically (e.g., through infusion), internally, etc. Cultured cells can be administered to a patient by any method of delivery, such as intravascularly, intracranially, intracerebrally, intramuscularly, intradermally, intravenously, intraocularly, orally, nasally, topically, or by open surgical procedure, depending upon the anatomical site or sites to which the cells are to be delivered. Cultured cells can be administered in an open manner, as in the heart during open-heart surgery, or in the brain during stereotactic surgery, or by intravascular interventional methods using catheters going to the blood supply of the specific organs, or by other interventional methods. The cells can be administered to various organs, such as the heart or brain. The methods of the subject invention contemplate intracerebral grafting of cultured cells to a region of the central nervous system (CNS), such as a region having sustained defect, disease, or trauma. Neural transplantation or "grafting" involves transplantation of cells into the central nervous system or into the ventricular cavities, or subdurally onto the surface of the host brain. The cells can be administered in isolation or as an active component in a pharmaceutical composition that also includes a pharmaceutically acceptable carrier, which can be solid, semi-solid, or liquid, for example. Preferably, cells are seeded in a stabilized CCAG scaffold and then implanted into a patient.

The terms "comprising", "consisting of", and "consisting essentially of" are defined according to their standard meaning and may be substituted for one another throughout the instant application in order to attach the specific meaning associated with each term.

As used herein, the term "copper capillary" or "copper capillaries" refers to the continuous parallel capillaries formed in alginate gels by diffusion of Cu2+ ions. These capillaries exhibit curved inner surfaces useful for seeding and propagating cells. The cross-section of the capillaries may be circular or non-circular.

As used herein, the term "culture", or grammatical variations thereof, is intended to denote the maintenance or cultivation of cells in vitro, including the culture of single cells. Cultures can be cell, tissue, or organ cultures, depending upon the extent of organization.

As used herein, the term "differentiated", or grammatical variations thereof, refers to those cells that maintain in culture all, or a substantial amount of, their specialized structure and function typical of the cell type in vivo. Partially differentiated cells maintain less than a substantial amount of their full complement of specialized structure and/or function. For example, the methods of the subject invention advantageously permit the culture of stem cells in an undifferentiated state, not developing any, or a substantial amount of, their full complement of specialized structure and/or functions.

As used herein, the term "electrostatically charged molecule" refers to any molecule possessing functional groups (e.g., carboxylic acid or amine residues) in a charged state (e.g., ionized or protonated).

As used herein, the terms "host" and "patient" are used interchangeably and intended to include humans and non-human animals. Accordingly, cells cultured according to the method of the subject invention can be utilized for veterinary purposes. The transplanted cells can be allografts, autografts, or xenografts, for example.

As used herein, the term "phenotype" refers to all the observable characteristics of a cell (or organism); its shape (morphology); interactions with other cells and the non-cellular environment (e.g., extracellular matrix); proteins that appear on the cell surface (surface markers); and the cell's behavior (e.g., secretion, contraction, synaptic transmission).

As used herein, the term "progenitor cell" (also known as a precursor cell) is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the terms "proliferate" and "propagate" are used interchangeably to refer to cell division.

As used herein, the term "stem cell" is an unspecialized cell that is capable of replicating or self renewal, and developing or giving rise to specialized cells of a variety of cell types. The product of a stem cell undergoing division is at least one additional stem cell that has the same capabilities of the originating cell. For example, under appropriate conditions, a hematopoietic stem cell can produce a second generation stem cell and a neuron. Stem cells include embryonic stem cells (e.g., those stem cells originating from the inner cells mass of the blastocyst) and adult stem cells (which can be found throughout the more mature animal, including humans). As used herein, stem cells are intended to include those stem cells found in animals that have matured beyond the embryonic stage (e.g., fetus, infant, adolescent, juvenile, adult, etc.). The list of tissues reported to contain stem cells is growing and includes, for example, bone marrow, peripheral blood, brain, spinal cord, umbilical cord blood, amniotic fluid, placenta, dental pulp, blood vessels, skeletal muscle, epithelia of the skin and digestive system, cornea, retina, liver, and pancreas.

As used herein, the term "stabilizing agent" refers to a compound, ion, or moiety that reacts with the CCAG so that the resulting stabilized CCAG maintains its mechanical properties in a cell culture or within a human or animal and the stabilized CCAG is non-toxic to its surrounding environments.

As used herein, the terms "treat", "treatment", or grammatical variations thereof, within the context of hosts, refer to interventions that merely alleviate symptoms of a pathological condition, such as disease or trauma, or can even be curative in nature. These terms are also intended to include prophylaxis. The host can be suffering from a pathological condition, such as disease or trauma, wherein cell therapy is desired to alleviate the symptoms of the pathological condition. For example, neural cells cultured according to the methods of the subject invention can be administered to alleviate the symptoms of a neurological condition, such as a cognitive deficit. Examples of such neurological conditions include, but are not limited to, Alzheimer's disease, Parkinson's disease, Huntington's disease, ischemia, and brain trauma.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

MATERIALS AND METHODS

2% w/v Alginate solution preparation. 4 g of KELTONE LV sodium alginate (ISP Alginates Inc.) was dispersed in 170 ml of deionized (DI) water in a 500-ml Erlenmeyer flask. The suspension was stirred with a stir plate at medium-high speed until a clear, homogenous solution is obtained. DI water was then added to the solution until the final solution volume is 200 ml yielding a 2% w/v solution of sodium alginate (manufacture's reported viscosity: 100-300 centipoise (cP)). The alginate solution was stirred for 2 hours and then let stand for an additional 2 hours to minimize solution bubbles. Solutions were either used immediately or stored for no more than a week at 4° C.

2% w/v Oligochitosan Solution Preparation. 2 g of oligochitosan were dispersed in 80 ml of DI water in a 250-ml Erlenmeyer flask. The suspension was then stirred vigorously until a clear, yellow-brown solution is obtained. DI water was then added to the solution until the final solution volume is 100 ml yielding a 2% w/v solution of oligochitosan. Solutions were either used immediately or stored for no more than a week at 4° C.

Petri Dish Preparation. A thin coat of alginate needs to be baked onto the petri dish to prevent gel separation from the vessel wall during growth. Five thin coats of freshly prepared 2% w/v alginate solution were smeared onto the entire inner surface and rim of a PYREX petri dish (9 cm diameter×2 cm height or 9 cm diameter×3.25 mm height). A few minutes for air-drying were allowed in between each coat. Once the 5 coats have been applied, the coated petri dish was baked in an oven heated at 120° C. for 10 minutes. The dish was then removed, allowed to cool and the procedure was repeated 3 additional times.

Preparation of Raw Copper Capillary Alginate Gel (RC-CAG). An alginate-coated petri dish was carefully filled to the brim, almost overflowing, with freshly prepared 2% w/v sodium alginate solution. A large KIMWIPE soaked with freshly prepared 1M copper sulfate solution was pulled taut like a drum using a needle hoop and brought down directly on top of the alginate filled petri dish. The entire surface of the alginate solution and rim of the petri dish were ensured to be in good contact with the soaked KIMWIPE. Over the course of 5-7 minutes at approximately 10-15 second intervals, 1-2 ml of 1M copper sulfate solution was dripped onto the soaked KIMWIPE now covering the alginate filled petri dish. The soaked KIMWIPE was then slowly and gently peeled off the alginate filled petri dish. A solid membrane contiguous with the rim of the petri dish ca. 1 mm thick should be completely covering the top of the alginate filled petri dish. This membrane, termed the primary membrane, was a little rough, approximately the color of the 1M copper sulfate solution and should contain no visible voids. Taking extreme care not to jar the gelling solution, the filled petri dish was transferred to a large covered tank. The tank's geometry allowed for a 1.5-2 cm submersion of an alginate filled petri dish in 700 ml of the 1M copper sulfate solution. The tank was slowly filled with 700 ml of 1M copper sulfate, covered and left undisturbed for 36 hours.

Preparation of Oligochitosan Stabilized Copper Capillary Alginate Gel (OCCAG). CCAG samples (3-5) cut into rectangles (1 cm×0.5 cm×0.5 cm) were placed into 50 ml centrifuge tubes. Freshly prepared oligochitosan solution (45 ml, 2% w/v) was then added to each, and the tubes were then placed on an orbital shaker for 17-19 hours. Next, the oligochitosan solution was poured off and the samples are rinsed three times with small volumes of DI water. DI water was then added (45 ml/tube), and the tubes were placed on an orbital shaker overnight. The DI water was fully exchanged at least once over the next 8-12 hours. Samples can now be stored in a small volume of DI water at 4° C. OCCAG samples must be thoroughly washed in complete cell culture medium before use in experimental studies. Oligochitosan stabilized CCAG samples were placed singly into the wells of 6-well cell culture plates. Three milliliters of complete cell culture media were then added and the plates are placed in a 37° C. incubator overnight. The media was then completely exchanged and the plates are returned to the incubator overnight. After this point, the scaffolds were ready for in vitro and/or in vivo experiments.

EXAMPLE 1

Stabilization of CCAG Scaffold with Ba(OH)$_2$

A CCAG scaffold was stabilized via ion exchange with Ba(OH)$_2$. Specifically, raw CCAG samples were placed individually into 15 ml of 0.05M Ba(OH)$_2$ and stirred on an earthquake shaker for one week. The Ba(OH)$_2$ solution was changed daily, and each step was conducted at room temperature (about 23° C.). During the first several hours of the exchange process, the raw CCAG samples changed in color from a light blue, due to Cu$^{2+}$, to a deep royal blue. When CCAG samples were initial submerged into 0.05M Ba(OH)$_2$ solution they floated due to a difference in density. Within minutes equilibrium was reached and the samples sank; this sinking was accompanied by the color change. The color change began at the disc edges and faces and proceeded toward the center of the sample. At anytime before completion of the diffusion process (12-24 hrs.), an inner core of light blue/blue-green color could be observed. If the raw samples were not washed thoroughly with DI water to remove excess Cu$^{2+}$ before submergence in the Ba(OH)$_2$ solution, a brownish-black, gelatinous precipitate formed sometime between 12-24 hours of submergence throughout the samples. This blackening was further enhanced during washing of the barium-stabilized CCAG in DI water. Soaking the barium-stabilized samples in MEM resulted in a total loss of color.

The above calorimetric changes can be explained by the formation of different copper compounds within CCAG samples during barium hydroxide processing. The initial color change from translucent sky blue to royal blue corresponded to the reaction of Cu$^{2+}$ ions with hydroxide ions to form copper hydroxide (see reaction 1) which is often described as a pale blue gelatinous water insoluble precipitate.

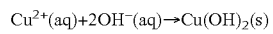

$$Cu^{2+}(aq) + 2OH^-(aq) \rightarrow Cu(OH)_2(s) \qquad 1$$

Although the term "pale" seems inconsistent with the above description, concentration and matrix effects presumably influence the apparent copper hydroxide color intensity.

The progressive blacking of the core was due to the progressive formation of copper II oxide (see reaction 2).

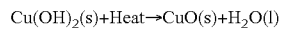

$$Cu(OH)_2(s) + Heat \rightarrow CuO(s) + H_2O(l) \qquad 2$$

Copper II oxide is often described as a black or golden brown insoluble precipitate formed by heating copper hydroxide. The heat released by the formation of copper hydroxide in the CCAG possible drove its own decomposition to copper II oxide within the gel.

Figure 14A:
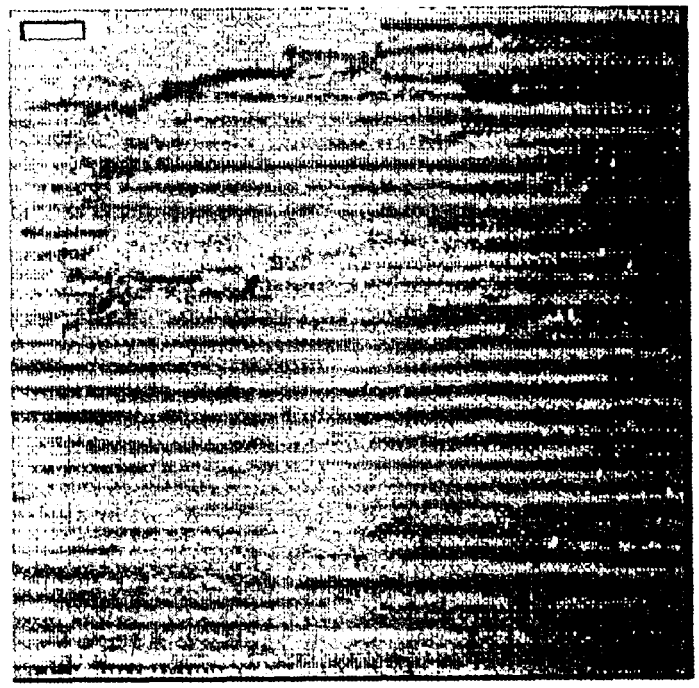
FIGS. 14A-14B are BCCAG optical micrographs.
Figure 14B:
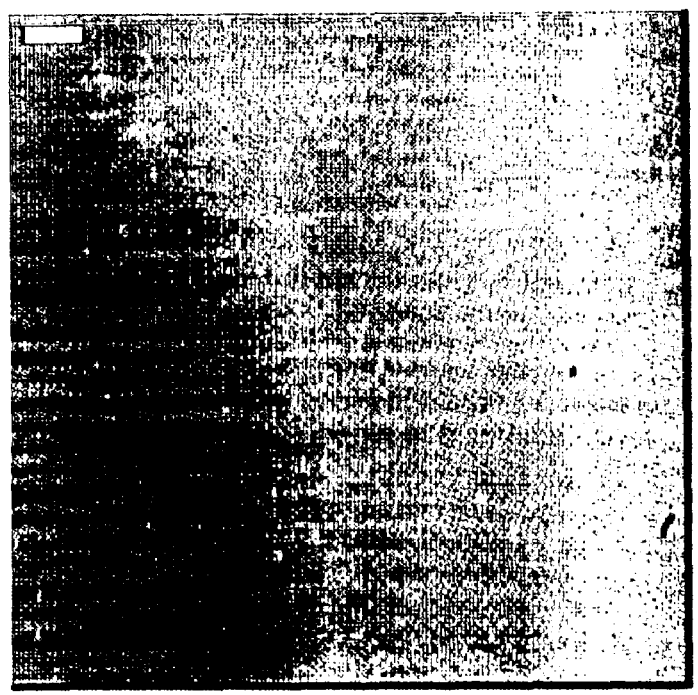

FIGS. 14A and 14B are representative micrographs showing brown and shimmering particles within BCCAG samples. The precipitate shown in FIG. 14A appears golden-brown (presumably due to lighting) and is the same formation responsible for the progressive blacking described in the scaffold synthesis section above. This datum further supports the claim that copper oxide has precipitated with the capillaries of BCCAG due to processing in barium hydroxide solution. The shimmering particles are believed to be insoluble barium sulfate and/or carbonate crystals formed within the walls of BCCAG during synthesis.

Freeze drying of the barium stabilized CCAG yielded a gel that maintained the circular capillary morphology but that was fragile and powdered if handled too much (FIGS. 15A and 15B). The representative EDS spectrum (FIG. 15C) indicates that BCCAG is mainly composed of carbon, oxygen, copper and barium. Strontium also appears in the spectrum, overlapping the same energy range as silicon. Silicon could be present but being masked by strontium which apparently came from the barium hydroxide solution. The small aluminum peak is possibly due to scatter from the SEM mount.

Figure 16A:
FIGS. 16A-16H show a higher magnification barium stabilized CCAG morphologic and compositional study.
Figure 16B:
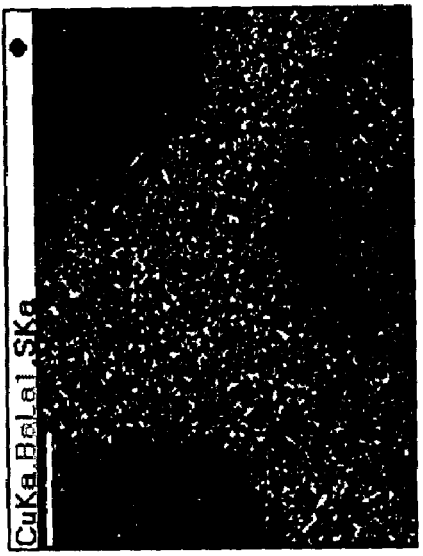
Figure 16C:
Figure 16D:
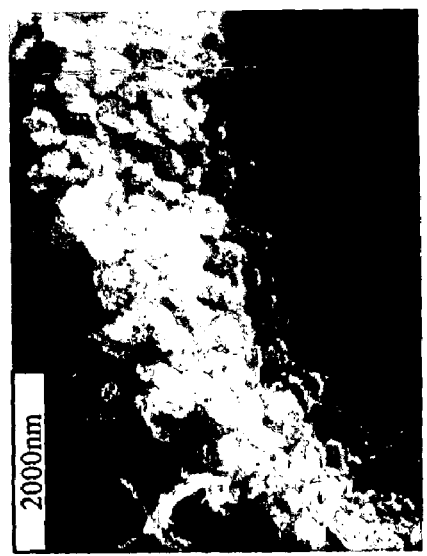
Figures 16E, 16F, 16G, 16H:
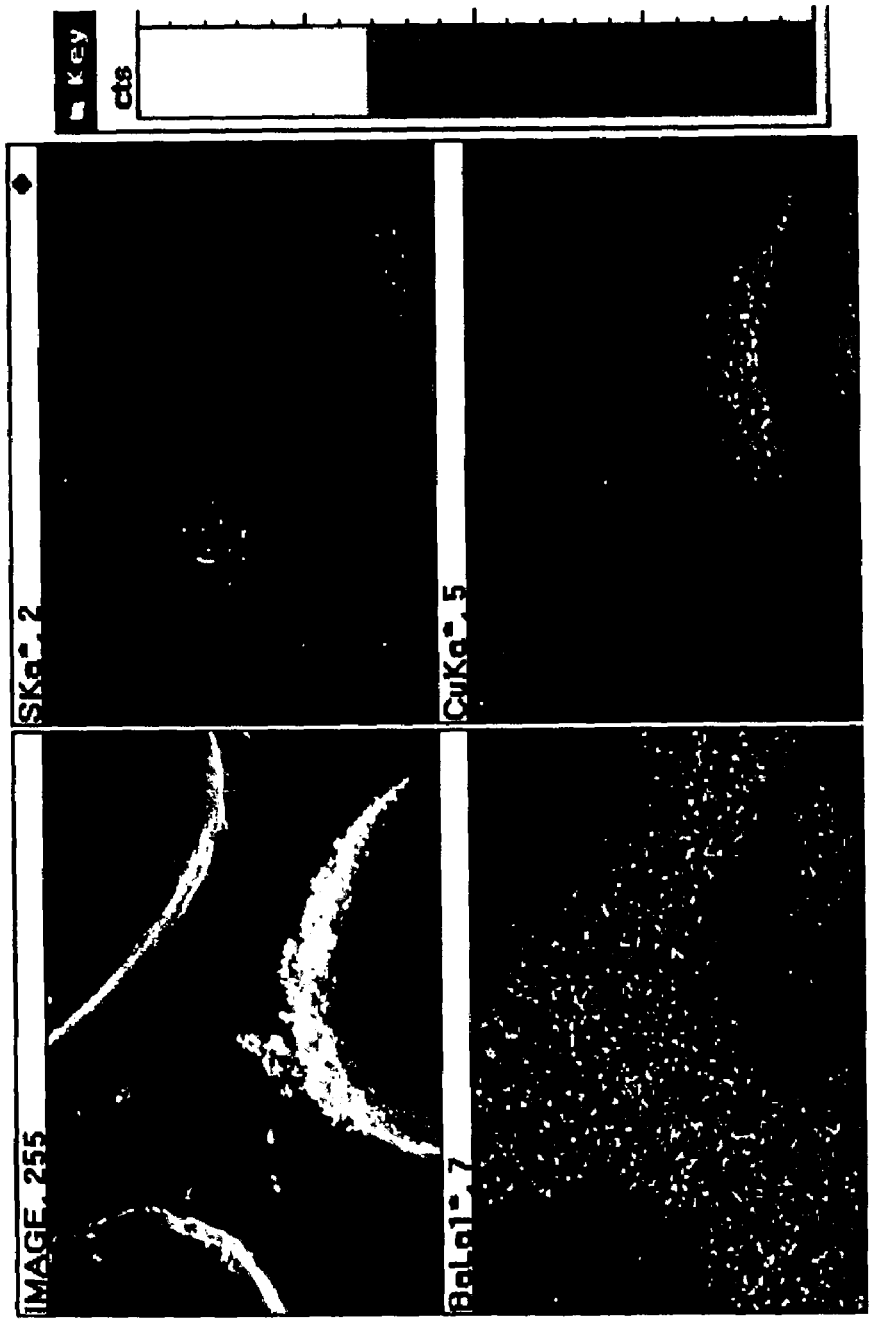

FIGS. 15D-15G, the barium stabilized CCAG X-ray map group, is markedly different from the RCCAG map group. Barium now appears homogenously distributed throughout BCCAG, supplanting copper. Strontium also appears uniformly distributed in a much smaller concentration. The majority of the copper signal is localized to the "bumpy" particles lining inner capillary diameters. FIGS. 16A and 16C are higher maginification SEI images of the copper-particles; FIG. 16B is the complementary BSE of 16A. FIGS. 16E-16H is an X-ray map group of the same area as FIG. 16A taken to more clearly illustrate the distribution of elements within barium stabilized CCAG. Sulfur rich areas also appear in this map group which are believed to correspond to the shimmering particles noted in barium stabilized CCAG optical microscopy (FIGS. 14A and 14B).

A complex series of physicochemical events occurs during barium hydroxide processing of raw CCAG. Upon submersion in the barium hydroxide solution, copper hydroxide begins to form in the outer surfaces and edges of the material. As the barium and hydroxide ions diffuse into the raw CCAG matrix and capillaries, $Cu^{2+}$ ions react with the OH– ions forming insoluble copper hydroxide at all material-solution interfaces. As the reaction proceeds, $Cu^{2+}$ ions at the interface are depleted, stimulating migration of $Cu^{2+}$ ions from within the material down their concentration gradient. Copper ions migrating to the material-solution interface react with the essentially infinite sink of solution hydroxide ions forming more insoluble copper hydroxide concentrated at the interface. Heat produced from the formation reaction is not dissipated efficiently within the raw CCAG sample, and thus drives the dehydration of the newly formed copper hydroxide to copper oxide over time. These ideas are not intended to apply to all copper within barium CCAG, because an examination of the barium CCAG X-ray map groups clearly shows copper within the BCCAG matrix.

Concomitantly, barium ion-exchanges with copper ions and/or forms new ionic crosslinks within the gel, stabilizing its structure. This exchange also presumably influences the migration of $Cu^{2+}$ ions to material-solution interfaces. Residual $SO_4^{2-}$ and dissolved $CO_3^{2-}$ ions also react with diffusing $Ba^{2+}$ ions forming insoluble salt crystals within the RCCAG matrix (see FIG. 16D). These crystals result in the "shimmering" optical micrographs discussed above.

EXAMPLE 2

Chitosan Stabilization of Scaffold

Figure 6:
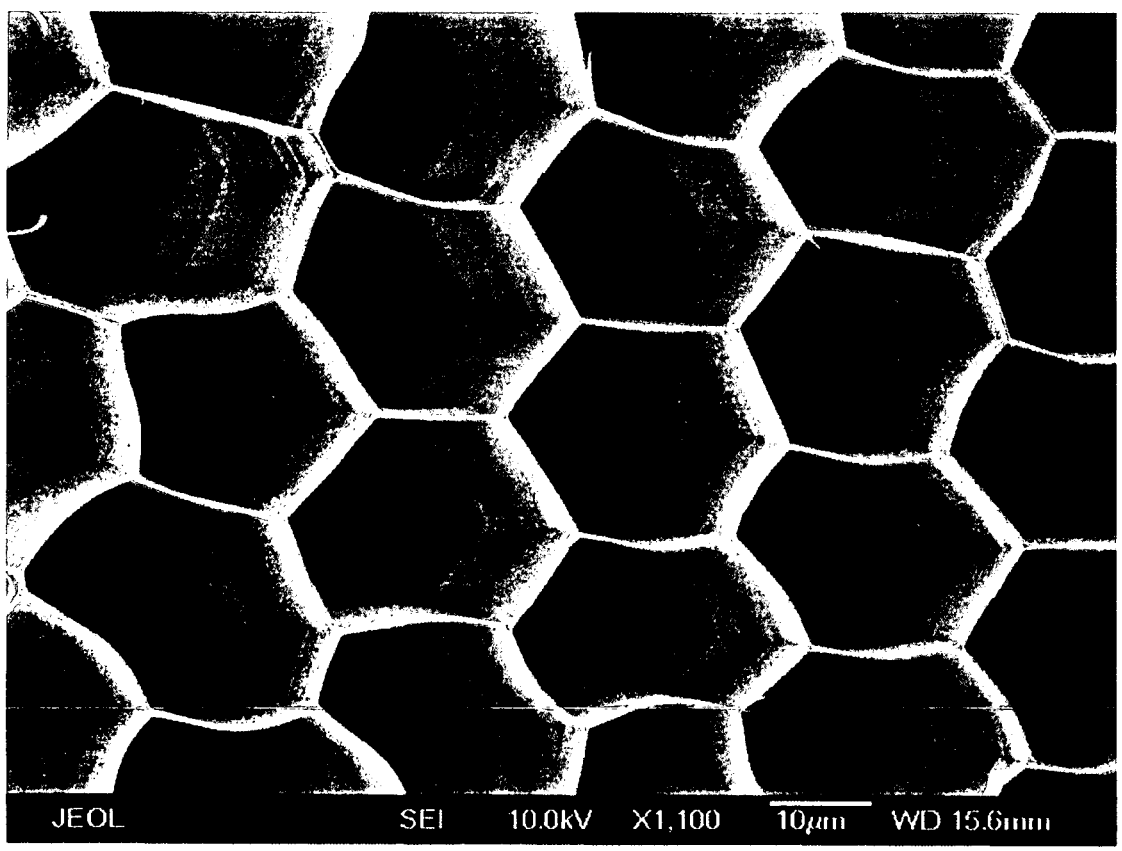
Figure 7:
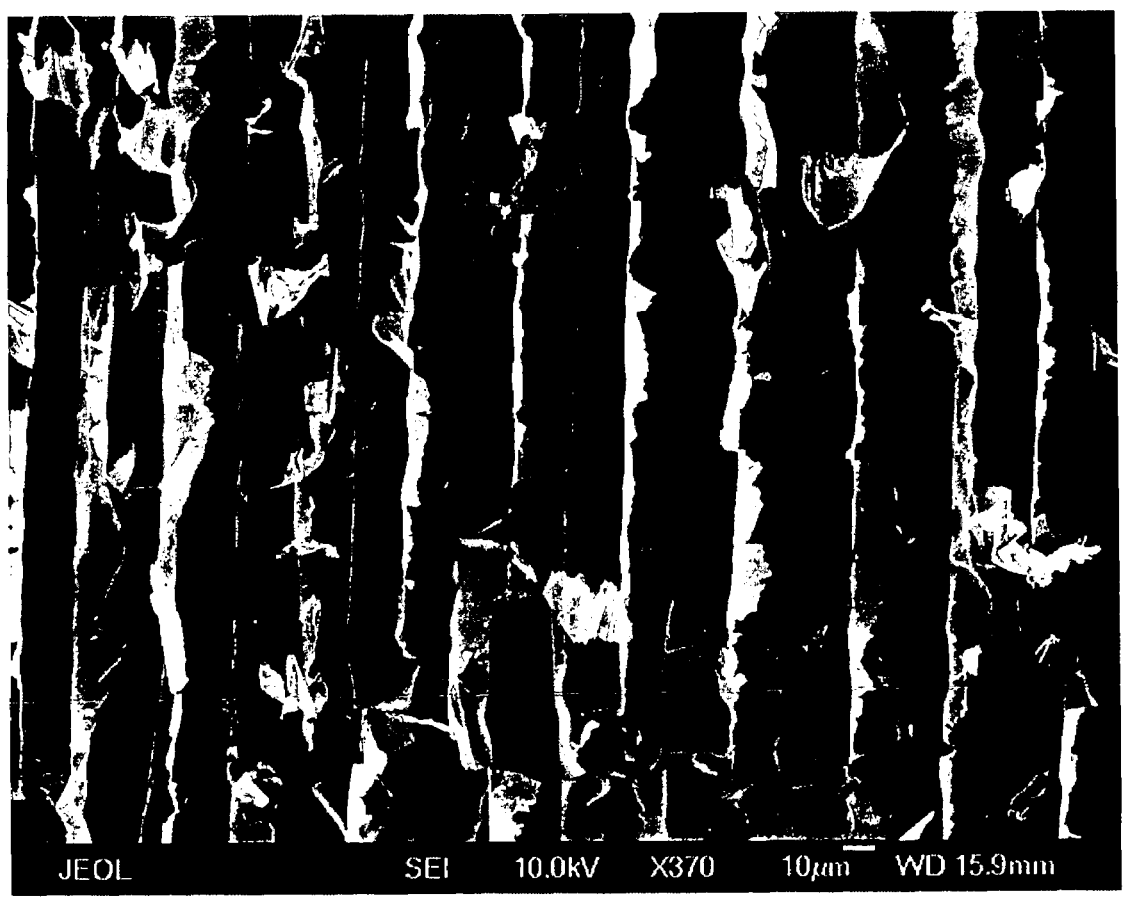
FIG. 7 shows a SEM image viewing capillaries of a raw CCAG sample parallel to the capillary axis.
Figure 8:
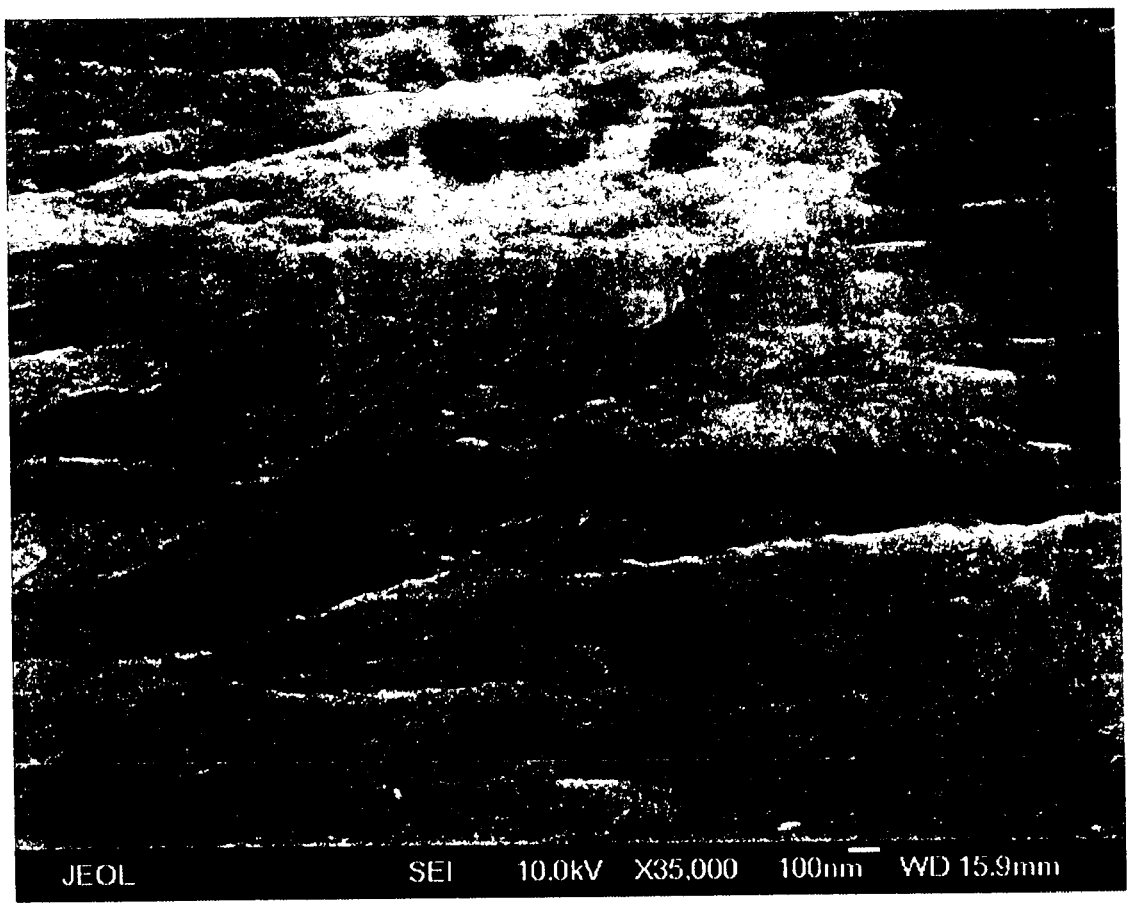
FIG. 8 shows a SEM image of a capillary wall of a raw CCAG sample.
Figure 9B:
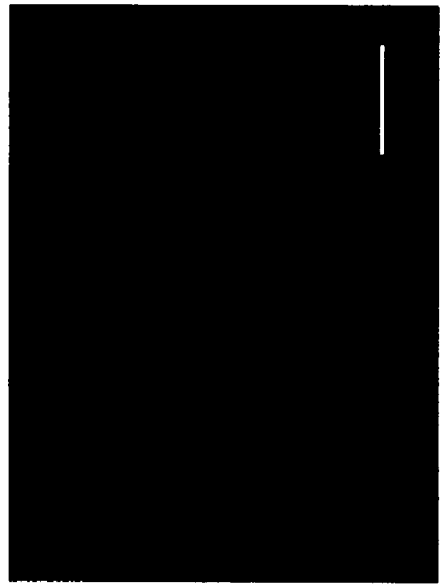
FIGS. 9A-9D show the growth of embryonic stem (ES) cells in CCAG.
Figure 9D:
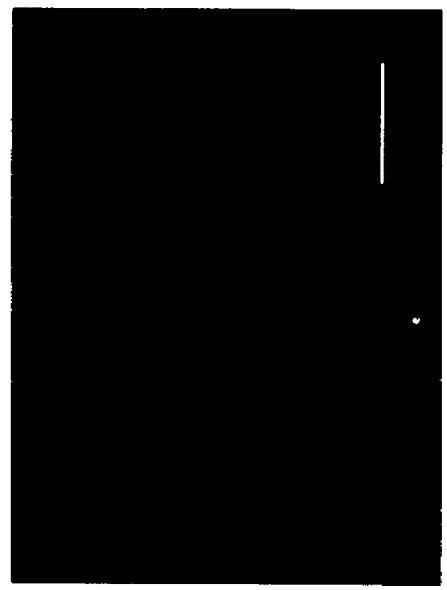
Figure 9A:
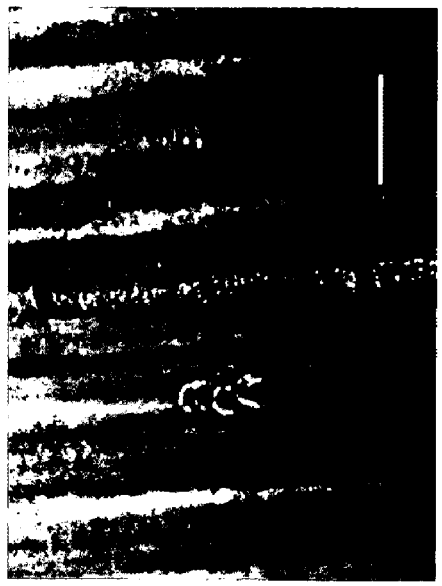
Figure 9C:
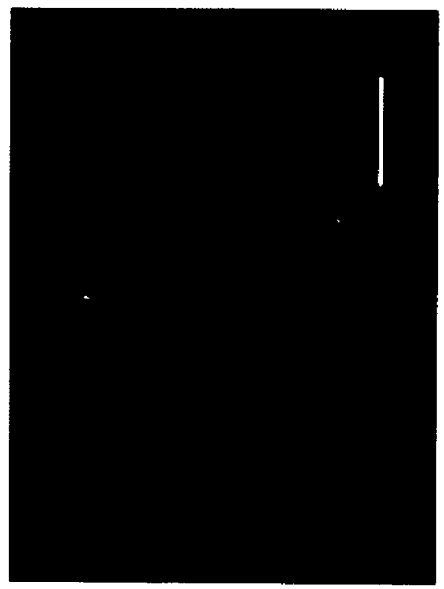

A chitosan-stabilized sample was also prepared using a flowcell-syringe pump setup as shown in FIG. 5. Thirty milliliters of 0.2% w/v chitosan solution was flowed at ca. 2 ml/min through the flowcell containing a raw CCAG sample disc. This process was repeated two additional times, and then the sample was placed in 14 ml of MEM and stirred overnight on an earthquake mixer. $Cu^{2+}$ diffused out of the chitosan-stabilized sample slower than out of raw CCAG samples. Also, the capillary morphology of the chitosan-stabilized sample changed from circular to non-circular upon copper removal with MEM as shown in FIG. 4. SEM images of capillaries of raw CCAG samples are shown in FIGS. 6-8.

Raw CCAG sample discs are placed singly in a flow cell. Freshly prepared chitosan solution (25 ml 0.02M acetic acid, 0.2% w/v) is flowed through the sample disc at 3 ml/min via a syringe pump. Next, DI water (10 ml) is flowed through the sample at the same flow rate. Freshly prepared alginate stock solution (2.5 ml, 2% w/v) is diluted 10-fold. The diluted alginate stock solution (25 ml, 0.2% w/v) is then flowed through the same sample disc at the 3 ml/min. DI water (10 ml) is then flowed through the sample at the same flow rate. The chitosan step is repeated an additional time to produce a 3 layer PEC; the entire process plus an additional chitosan step is repeated to produce a 5 layer PEC. The PEC samples are then stored in DI water (15 ml/sample) at 4° C. for later use.

EXAMPLE 3

SEMS/EDS Analysis

The large depth of field of a SEM provided for excellent depictions of the 3-dimentional structure of the sample scaffolds. Compositional information via EDS was collected at essentially the same time with a LOD ca. 1000 ppm. The technique was relatively simple and straightforward with the aid of a software package. The samples were, however, permanently changed due to the drying and conductive coating procedures required for SEM examination.

Freeze-dried samples produced previously were mounted separately onto aluminum SEM stubs with double-sided carbon tabs. The mounted specimens were then carbon coated and stored until analyzed in a desiccator. All samples were analyzed using a JEOL JSM-6400 SEM equipped with an Oxford EDS system and a LINK ISIS software package version 3.35. All samples were analyzed at 20KeV accelerating voltage as preliminary results have shown that good images can be easily obtained at this setting. Also, this accelerating voltage should be more than sufficient to observe all X-ray peaks of interest with EDS. All planar morphometric data was collected using the image analysis component of the LINK ISIS software package. Table 1 details the emission energies for expected elements.

TABLE 1

| X-ray Emission Energies for Selected Elements (KeV) | | | | |
|---|---|---|---|---|
| Element | Kα | Kβ | Lα | Lβ |
| C | 0.27737 | — | — | — |
| N | 0.39236 | — | — | — |
| O | 0.52492 | — | — | — |
| Ca | 3.69061 | 4.01286 | 0.34128 | 0.34498 |
| Cu | 8.04139 | 8.90559 | 0.92971 | 0.94986 |
| Ba | — | — | 4.46641 | 4.82770 |

Methods are being explored to evaluate the concentration of nitrogen in the samples.

EXAMPLE 4

Oligochitosan Stabilization of CCAG Scaffold

Oligochitosan stabilized CCAG was synthesized according to the methods discussed above. Oligochitosan stabilized CCAG was inhomogeneously colored in cross-section, composed of a yellowed outer surface with a blue-green core. This inhomogeneity is likely the result of differential crosslinking of the exterior and core by the 2% w/v oligochitosan solution.

Apparently, a more densely crosslinked skin of alginate:oligochitosan PEC formed around samples of CCAG.

Overexposure or overreaction is a concern and possibility for any chemical crosslinking procedure of polymeric materials and CCAGs are no exception. The oligochitosan is a multifunctional crosslinker forming ionic rather than covalent bonds. The electrostatic bonding between the CCAG or barium stablized CCAG and oligochitosan happens essentially instantaneously. Slightly-moderately overexposed rectangular samples began to round at the corners and distort as the overcrosslinked PEC skin contracted on the low modulus gel core. This skin was also darkly stained brown which negatively impacted its optical qualities. It was also found in an early set of experiments that CCAG stiffened, turned dark brown and profoundly shrunk when severely overreacted in an excess of 2% w/v oligochitosan solution (reaction times ≧24 hours). Syneresis of the gel likely accompanied these profound changes.

A reaction time range of 17-19 hours was used to stabilize both CCAG and barium stabilized CCAG with 2% w/v oligochitosan solution. This exposure time resulted in no significant change in the materials' original size and morphology, and the materials were only slightly yellowed in color after the reaction. This synthesis however failed during the cell culture media wash.

Media washing is technically the final step in scaffold processing because material changes occur during the process. All of the copper present in the scaffolds as free ions or otherwise appears to be removed with successive washes in media. This effectively dissolved the water insoluble copper hydroxide and oxide particles present in barium stabilized CCAG. Free copper ions were also apparently leached or chelated serving to decolorize the scaffold. The result was a translucent scaffold colored the same as the phenol red spiked media itself. This result was great because it facilitated sterilization and the use of advance microscopic techniques to observe the cells in situ, alive and dynamic. The oligochitosan stabilized CCAG results were similar to the barium stabilized CCAG results, but barium oligochitosan stabilized CCAG collapsed and stiffened reminiscent when washed in media reminiscent of the earlier overcrosslinked CCAG and consequently was never used in cell culture experiments.

Figure 17A:
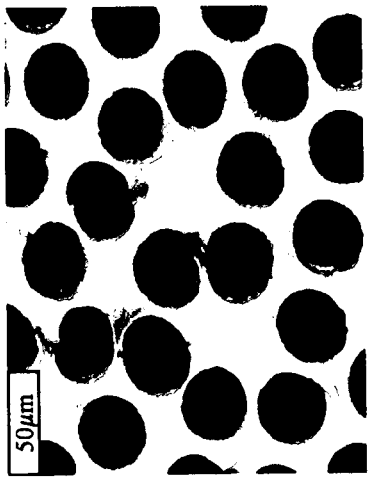
FIGS. 17A-17G show a summary of OCCAG SEM/EDS and X-ray mapping data.
Figure 17B:
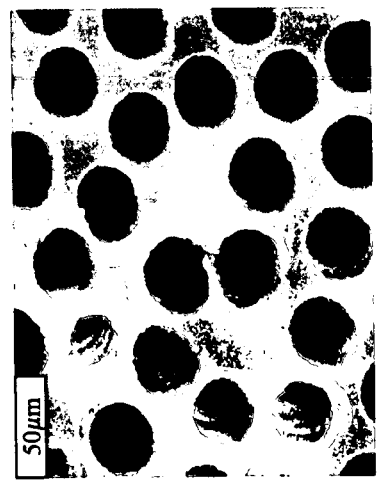
Figure 17C:
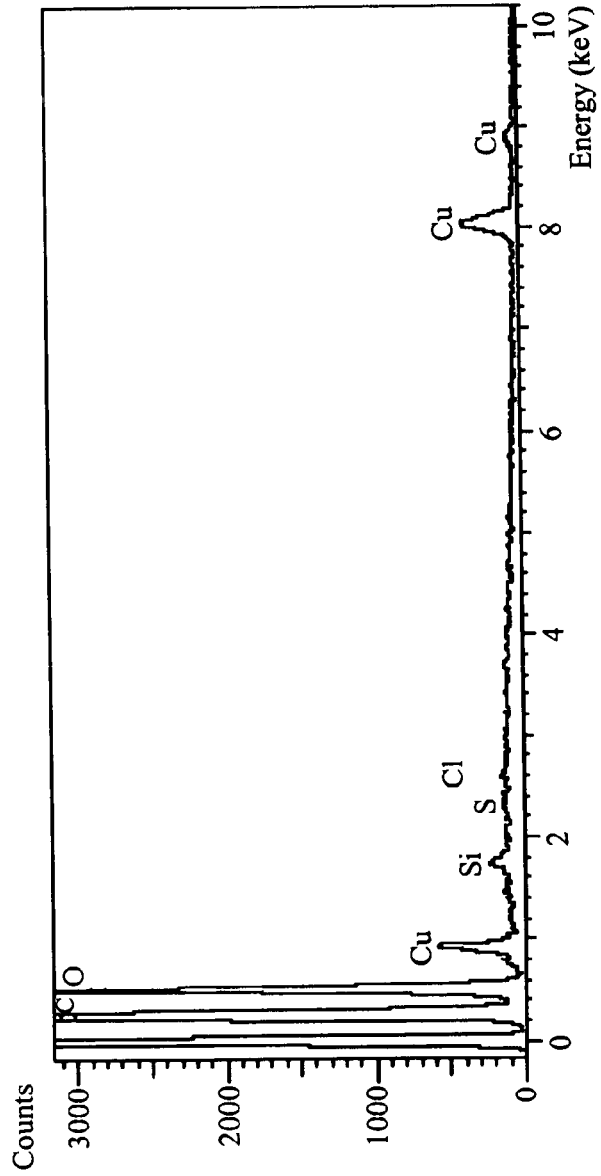
Figures 17D, 17E, 17F, 17G:
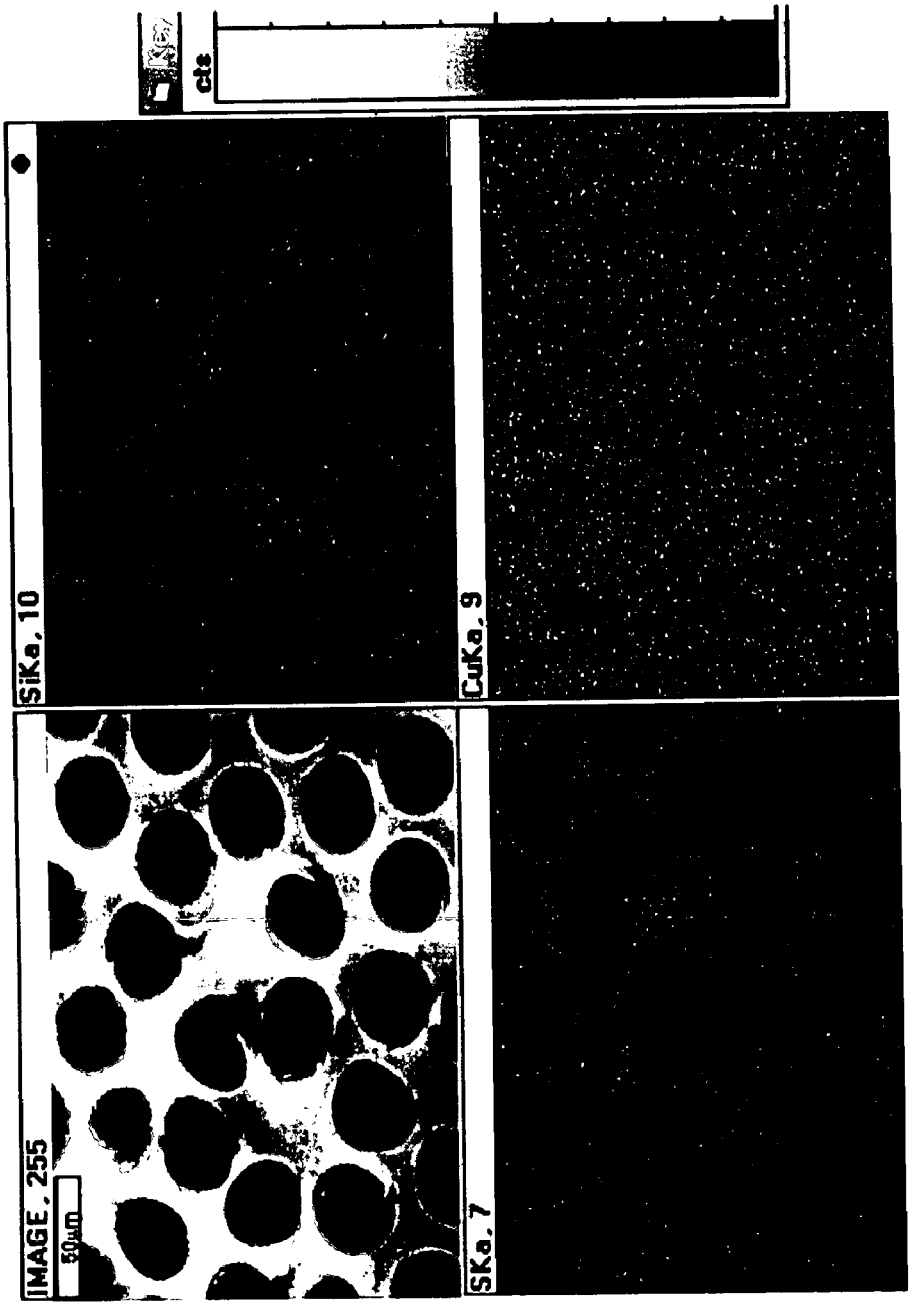
Figure 18:
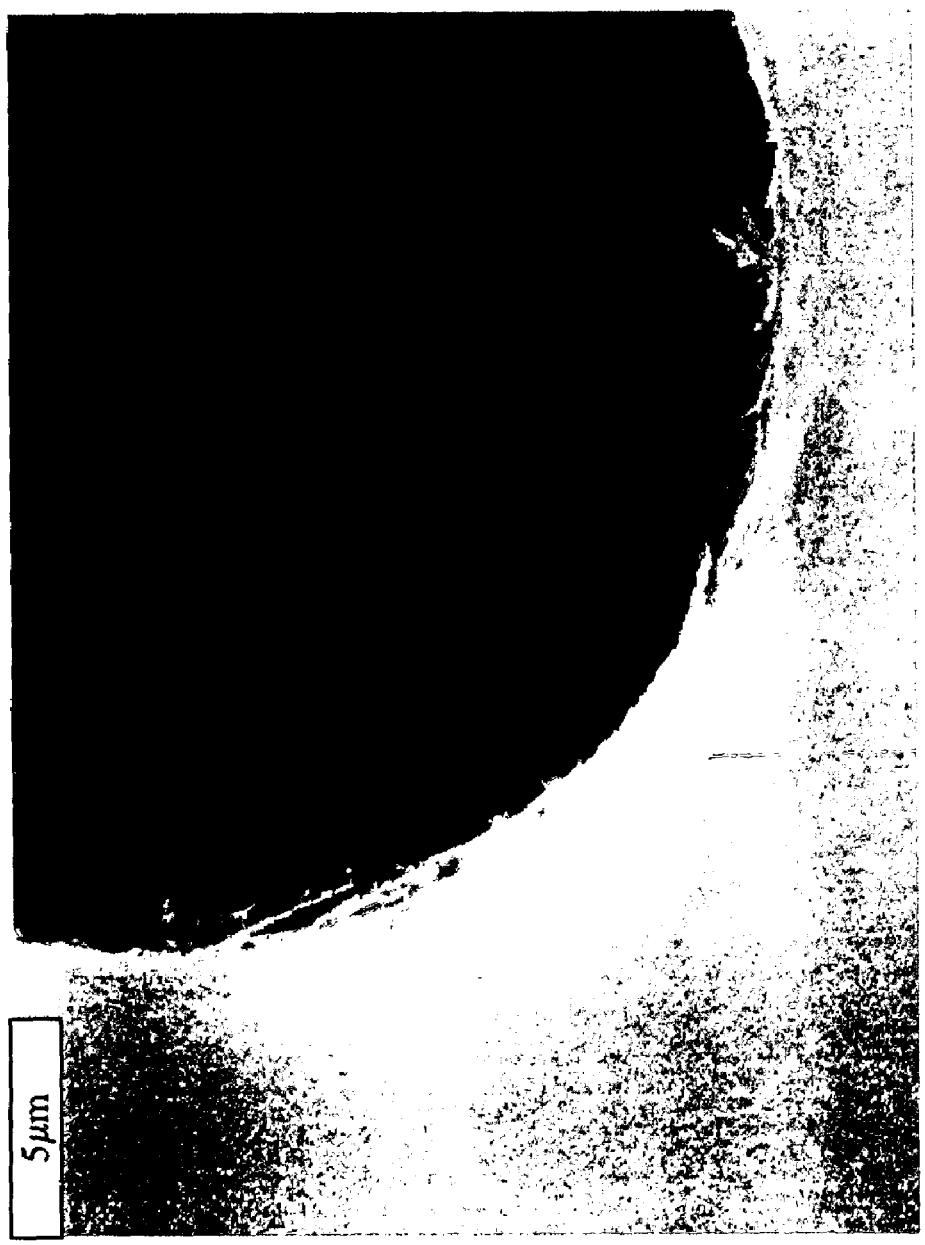
FIG. 18 shows a 4000× secondary electron image highlighting the "hairy" OCCAG surface character.

FIG. 17A is a summary of the representative oligochitosan stabilized CCAG SEM/EDS and X-ray mapping. FIG. 17A shows that oligochitosan stabilized CCAG has also retained circular capillaries, but the material's surface appears "hairy". This surface character can be more easily seen in the higher magnification SE image shown in FIG. 18. The striated layer structure of the raw CCAG has also been preserved. The oligochitosan stabilized CCAG EDS spectrum (FIG. 17C) appears similar to the raw CCAG EDS spectrum shown earlier with the addition of small amounts of chlorine. Closer inspection of FIG. 17C shows a much higher carbon and oxygen intensity as well as a reduced copper intensity in contrast to raw CCAG. This is probably the due to oligochitosan processing.

The oligochitosan is a polymeric crosslinker composed mainly of carbon and oxygen. It ionically crosslinks raw CCAG through a positively charged amine functionality from the surface in. Hence, oligochitosan processing results in a carbonaceous film on the surface of oligochitosan stabilized CCAG which would contribute to the higher carbon and oxygen intensities, as well as damping the measured copper intensity. The amine residues of oligochitosan could also have leached $Cu^{2+}$ ions from the raw CCAG, during the 2% w/v oligochitosan solution processing, further contributing to the drop in measured copper signal.

EXAMPLE 5

Controlling Stem Cell Fate Using Biomaterial Scaffolds

B5/GFP embryonic stem (ES) cells, constitutively expressing green fluorescent protein (GFP), were seeded in CCAG and cultivated for 4 days in ES-maintenance medium containing LIF. ES cells proliferated in the CCAG and were forced to line up along with micro-capillary structure as illustrated in FIGS. 9A-9D.

Figure 10:
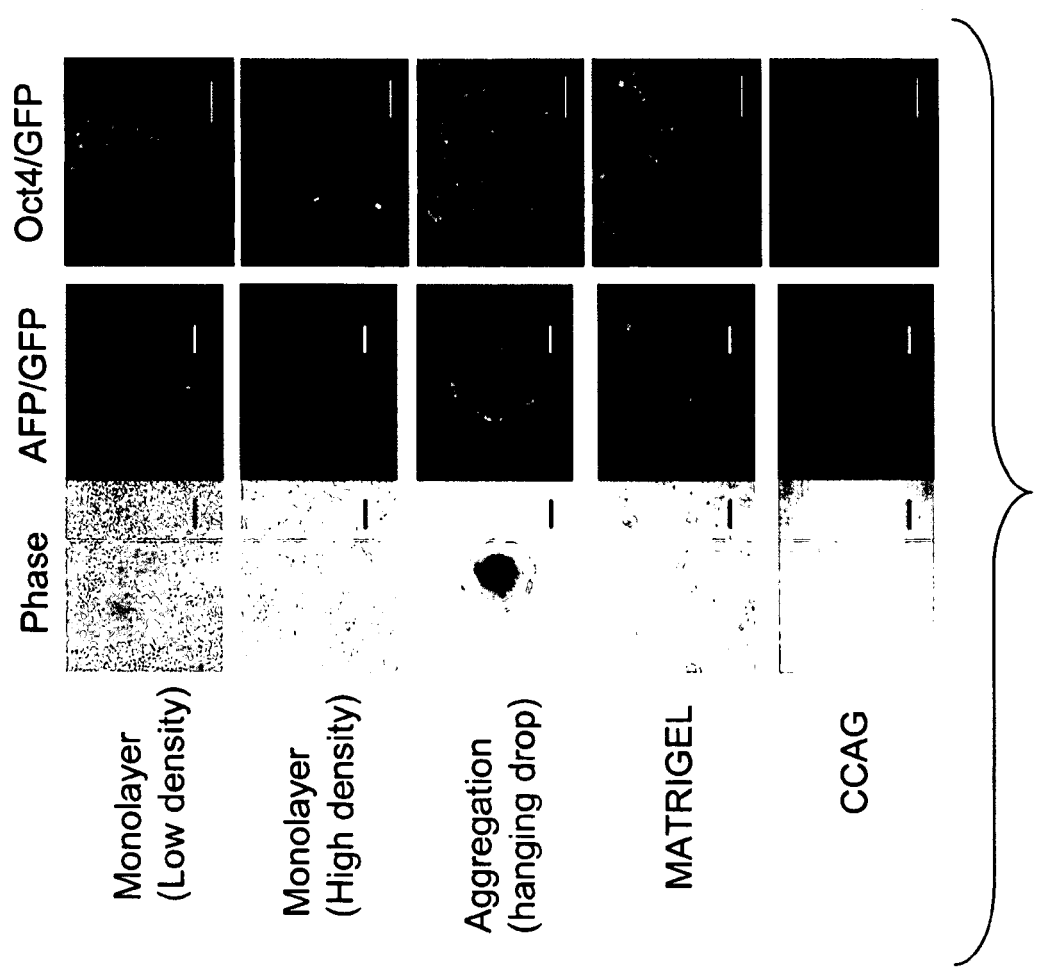
FIG. 10 shows monitoring of α-fetoprotein (AFP) and OCT-4 expression during ES differentiation in CCAG and other culture conditions.
Figure 11:
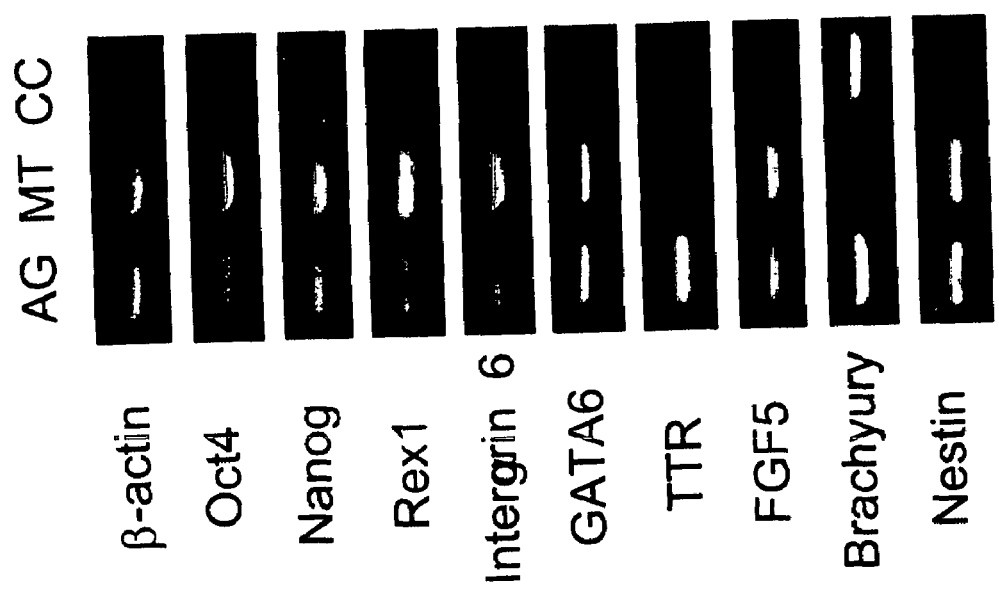
FIG. 11 shows embryonic stem (ES) cells exclusively expressed brachyury in CCAG.

To monitor the α-fetoprotein (AFP) and Oct-4 expression during ES cell differentiation, AFP/GFP ES cells were cultivated without LIF for 4 days in the conditions shown in FIG. 10. Oct4/GFP ES cells were cultivated in the same conditions as AFP/GFP ES cells. Primitive endoderm specification induced by cell aggregation was completely blocked in CCAG (FIG. 10; middle panel). Of interest, ES cells lost Oct-4-promoter derived GFP expression in CCAG (FIG. 10; right panel), indicating that ES cells were differentiating into other lineages in CCAG. Advantageously, ES cells exclusively expressed brachyury in CCAG (FIG. 11).

As illustrated in FIG. 12, ES cells lose pluripotency and are directly differentiated into early mesoderm phenotype when cultivated in CCAG.

Three ES cell lines were used in the study. Afp/GFP ES cells were previously described to monitor visceral endoderm differentiation (Hamazaki, T et al. *J. Cell. Sci.*, 2004, 117 (Pt23):5681-5686). B5/EGFP ES cells were kindly gifted from Dr. Andras Nagy (Hadjantonakis, A. K. et al. *Mech. Dev.*, 1998, 76(1-2):79-90), Nanog βgeo ES cells were kindly gifted from Dr Shinya Yamanaka (Mitsui, K. et al. *Cell*, 2003, 113(5):631-642). To monitor Oct4 expression by GFP, we generate Oct4 promoter-GFP transgenic ES cells (Oct4/GFP ES cells) from Nanog βgeo ES cells. Briefly, the vector containing green fluorescent protein under control of the Oct4 gene promoter was kindly gifted from Hans R. Scholer (Yoshimizu, T. et al. *Dev. Growth Differ.*, 1999, 41(6):675-684). The Oct4-GFP plasmid were co-transfected with pTK-Hyg (Clontech, Palo Alto, Calif.) into Nanog βgeo ES cells by using Fugene 6 (Roche, Indianapolis, Ind.) and selected with hygromycin B (200 μg/ml) (Invitrogen, Carlsbad, Calif.). After two weeks selection, GFP positive hygromycin B resistant clones were picked up.

Murine ES cells were maintained in an undifferentiated state on gelatin-coated dishes in Knock-out DMEM (GIBCO BRL, Grand Island, N.Y.) containing 10% knockout serum replacement (GIBCO BRL), 1% fetal bovine serum (Atlanta biologicals, Norcross, Ga.), 2 mM L-glutamine, 100 units/ml penicillin, 100 μg/ml streptomycin, 25 mM HEPES (GIBCO BRL), 300 μM monothioglycerol (Sigma, St. Louis, Mo.), and 1000 unit/ml recombinant mouse LIF (ESGRO) (Chemicon, Temecula, Calif.).

To initiate differentiation, undifferentiated ES cells were dissociated by using 0.25% trypsin/EDTA (GIBCO BRL). ES cells were suspended in IMDM, supplemented with 20% fetal bovine serum (Atlanta biologicals), 2 mM L-glutamine, 100 units/ml penicillin, 100 μg/ml streptomycin (GIBCO BRL), and 300 μM monothioglycerol (Sigma). ES cells were cultivated in the following conditions; 1) CCAG scaffold: To seed ES cells into 1 $cm^3$ CCAG, total 200 μl of the cell suspension ($1 \times 10^6$ cells/ml) were applied from the one end of the OCCAG capillaries while applying suction from the other end of the capillaries. Seal the both ends of the scaffold by 10% agar/PBS. 2) Cell aggregation: aggregation of ES cells was induced by making hanging drops on lid of petri-dish (2000 cells/drop) (Hamazaki, T et al. *J. Cell. Sci.*, 2004, 117(Pt23):5681-5686). 3) monolayer culture: tissue culture plates were coated with 0.1% gelatin (Specialty Media, Phillipsburg, N.J.). ES cells were plated the dishes with 1000 cells/cm$^2$ or 5000 cells/cm$^2$. 4) Matrigel: the cell suspension were mixed with Matrigel 1:1 ratio into 3×10$^5$ cells/ml final density (BD biosciences, Franklin Lakes, N.J.). 5) The cells were fixed with 3.8% fomaldehyde/PBS for 15 minutes at room temperature. Hoechst were used for nuclear staining.

Cells were dissociated with 0.25% trypsin/EDTA. Dead cells were stained with propidium iodide. The flow cytometry was performed on FACS Sort (BD biosciences). Data of 30,000 cells were recorded using CellQuest Acquisition software (BD biosciences).

Total RNA was extracted by using RNA aqueous kit (Ambion Inc. Austin, Tex.). cDNA was synthesized by using SuperScript II first-strand synthesis system with oligo (dT) (GIBCO BRL). PCR was performed by using Taq DNA polymerase (Eppendorf, Westbury, NY). For each gene, the DNA primers were originated from different exons to ensure that the PCR product represents the specific mRNA species and not genomic DNA.

Figure 20:
FIG. 20 is a confocal microscope image of live GFP-3T3 cells seeded within an oligochitosan stabilized CCAG scaffold at day 2 in culture. Scale bar=200 μm.
Figure 22:
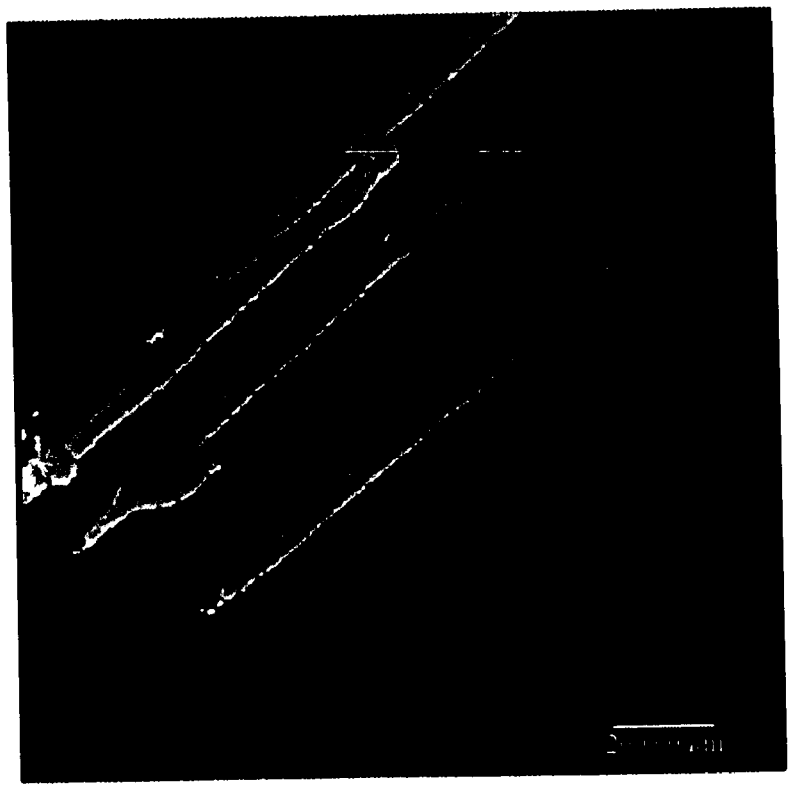
FIG. 22 is a confocal microscope image of live GFP-mES cells seeded within an OCCAG scaffold at day 7 in culture. Scale bar=200 μm.
Figure 21A:
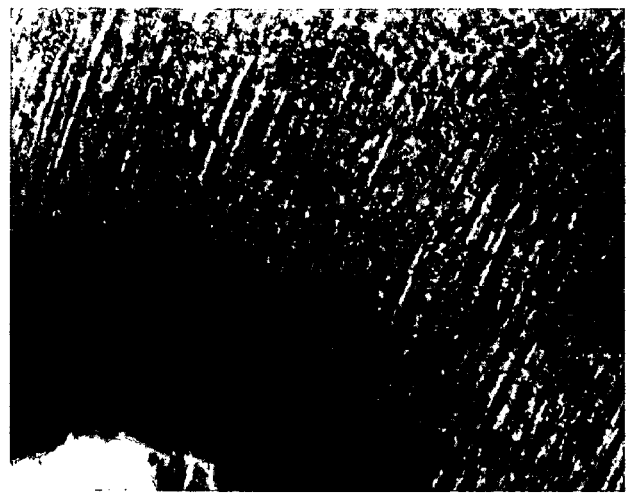
FIGS. 21A-21F show phase contrast and complementary fluorescence microscope image series of GFP-mES cultured in oligochitosan stabilized CCAG over nine days.
Figure 21B:
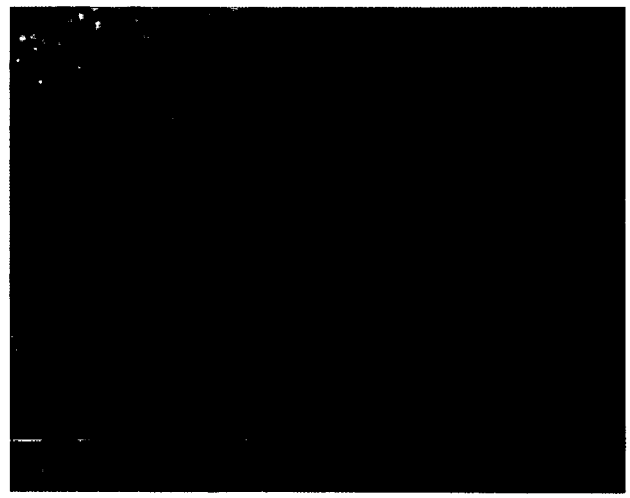
Figure 21C:
Figure 21D:
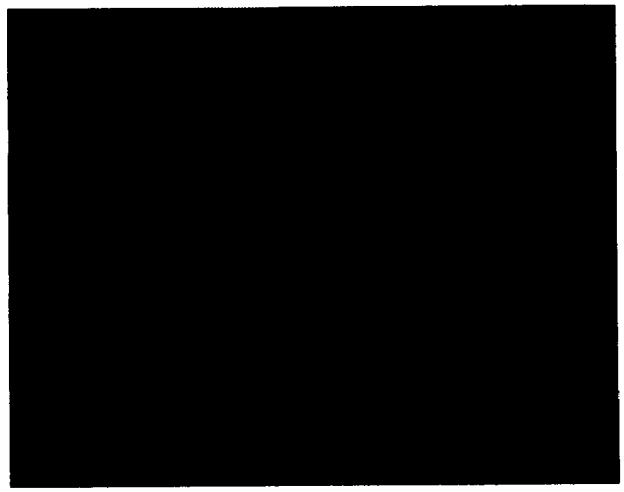
Figure 21E:
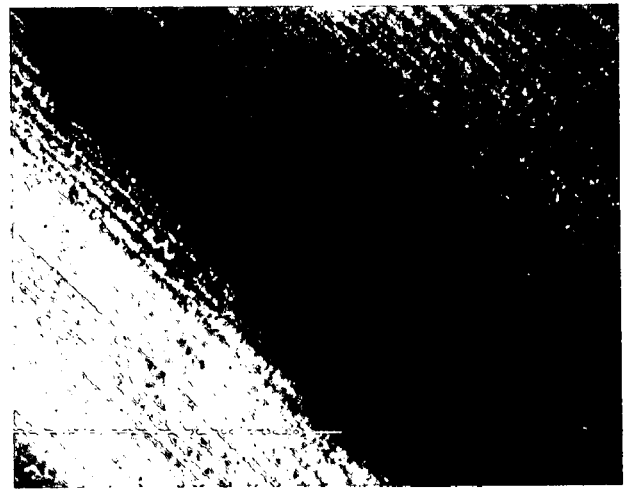
Figure 21F:
Figure 23:
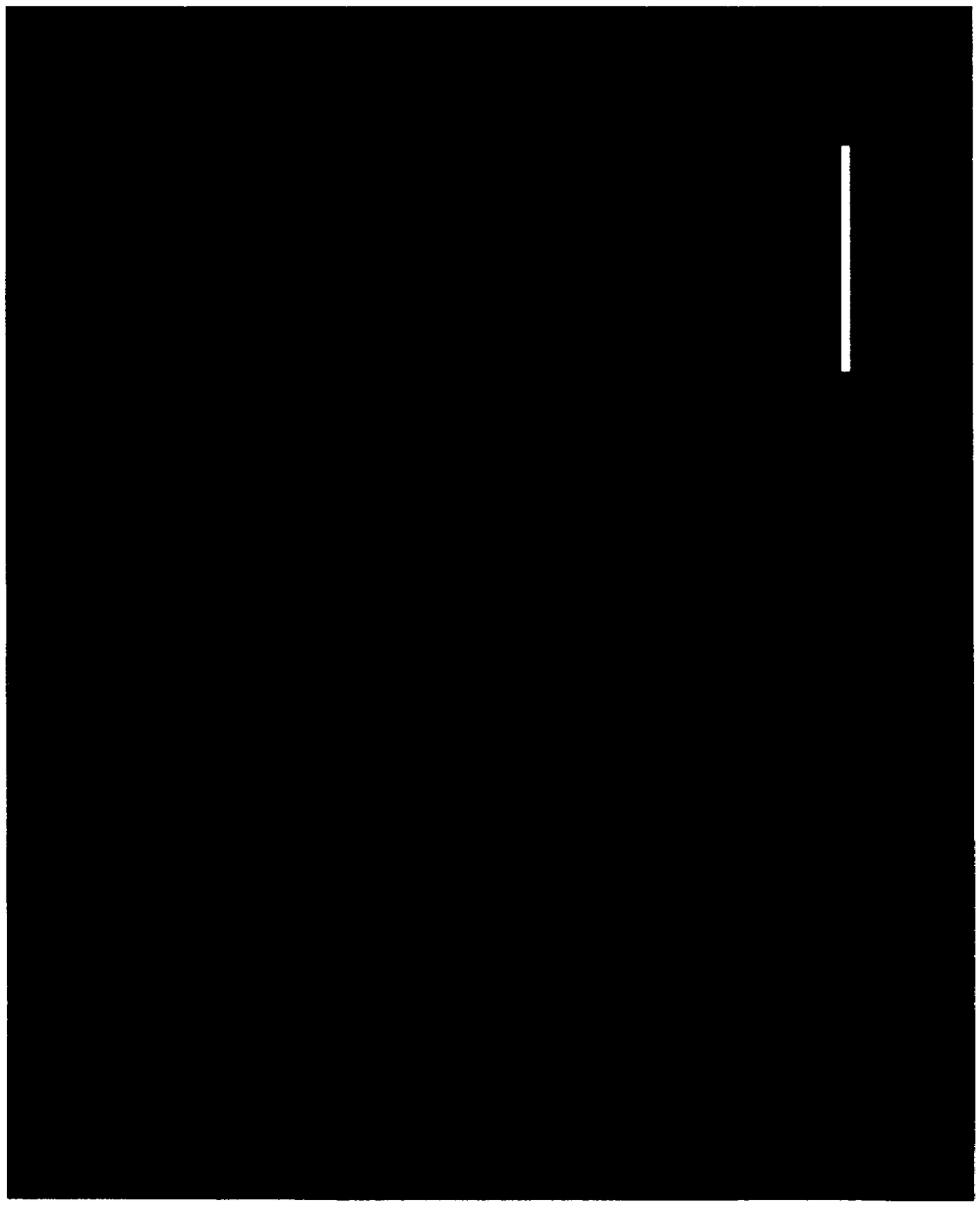
FIG. 23 is a fluorescence microscope image showing Hoechst stained nuclei of mES cells in an OCCAG capillary at day 4 in culture. Scale bar=75 μm.
Figure 24A:
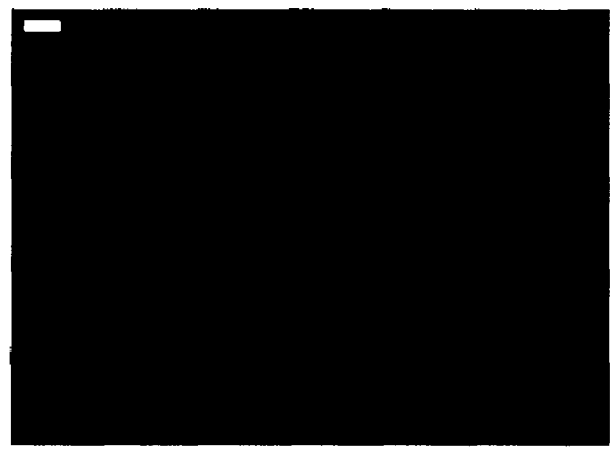
FIGS. 24A-24I show fluorescence microscope image series comparing the growth of GFP-mES cells in OCCAG scaffolds cultured in maintenance (M) or differentiation (D) media or a combination (M/D) over 4 days.
Figure 24B:
Figure 24C:
Figure 24D:
Figure 24E:
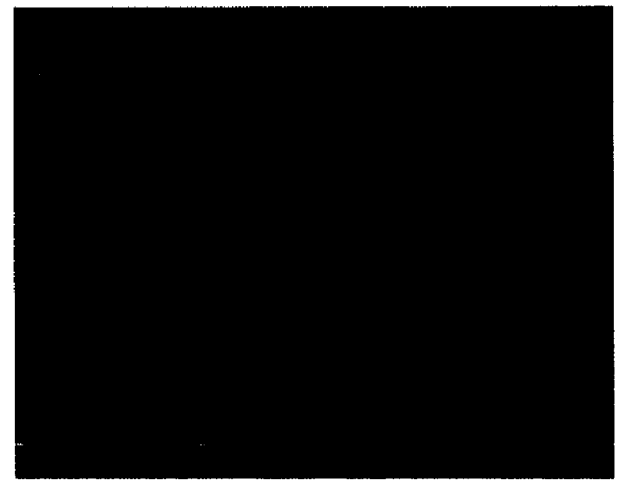
Figure 24F:
Figure 24G:
Figure 24H:
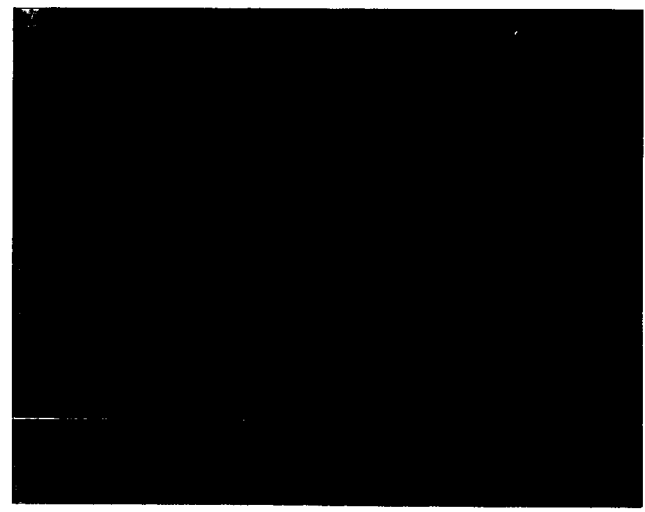
Figure 24I:
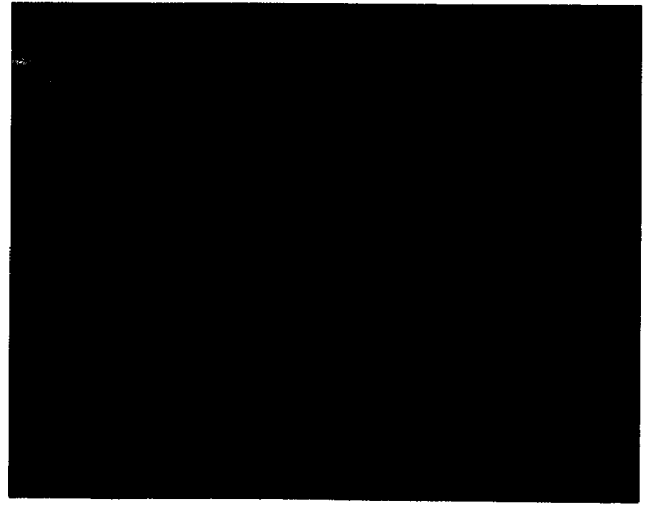

GFP-3T3 cells were initially chosen because they are robust, highly proliferative cells that were in good supply. Also, fibroblast migratory behavior has been reported on previously, and it was hoped that this behavior would be observed for direct comparison. Unfortunately, the GFP-3T3s available appeared to have the same diameter as the capillaries (~25 μm) and were not easily seeded into the oligochitosan stabilized CCAG scaffolds. This significantly limited the possible experimental work. FIG. 20 is a representative micrograph from an early GFP-3T3 study.

The relative clarity and translucence of the oligochitosan stabilized CCAG scaffold provided for reasonable good fluorescent and confocal images. The confocal video shows the morphology of GFP-3T3 cells up to ca. 100 μm deep (perpendicular to the capillary long axis) in the scaffold after two days in culture. Cells within capillaries usually appear deformed, taking on a pill-like shape. Multicellular aggregates appear clumped on the outer surface of the oligochitosan stabilized CCAG sample. This possibly indicates that oligochitosan stabilized CCAG is not very adhesive to cells as they prefer clump together rather than attach and spread on the materials surface. Cells confined within the capillaries typically did not survive more than 2-3 days and did not appear to proliferate. Large vacuous regions observed within the GFP-3T3s were also taken as a sign of poor cell health. It was then decided to switch to a different GFP expressing cell line.

In Vitro Study: Green Fluorescing Mouse Embryonic Stem Cells (GFP-mES)

Mouse embryonic stem cells are ~12 μm in diameter, ca. half that of the GFP-3T3s used above. It was therefore hoped that since the cells would no longer be squeezed into capillaries, they would survive and proliferate better (FIGS. 21-24).

Evaluation of Cell Growth, Survival and Morphology vs. Time

FIGS. 21A-21F shows phase contrast and complementary fluorescence micrographs documenting the survival, proliferation and morphology of GFP-mES cells cultured in OCCAG scaffolds over nine days. Since the GFP-mES cells constitutively expressed GFP, expression past 36 hours was taken as an indicator of cell viability. The cells usually seeded as small groups lined up in the capillaries (see FIGS. 21A and 21B).

At day 6, the cells had proliferated heartily and formed cylindrically structures within a few OCCAG capillaries. The cells had proliferated so well in some cases that they had escaped from the ends of capillaries and clumped into spherical structures (see FIG. 21D). These "Papillon" cell structures were judged to resemble embryoid bodies, a formation seen regularly in ES cell culture. Day 9 shows an extension of the behavior observed at day 6 with more capillaries filled. A group of cellular bulges seen in the central portion of FIG. 21F toward the top possibly shows the expansion of cells out of their initial capillary.

EXAMPLE 6

Target Cells

There are over 200 cell types in the human body and the methods of the present invention are useful in proliferating any of these cell types, therapeutic, manufacturing, or other purposes. Examples of cell types that can be proliferated using methods of the present invention are listed in the table below. Other examples of cell types that can be proliferated are disclosed herein.

TABLE 2

Examples of Target Cells

Keratinizing Epithelial Cells keratinocyte of epidermis
basal cell of epidermis
keratinocyte of fingernails and toenails
basal cell of nail bed
hair shaft cells
   medullary
   cortical
   cuticular
hair-root sheath cells
   cuticular
   of Huxley's layer
   of Henle's layer
   external
hair matrix cell Cells of Wet Stratified Barrier Epithelia surface epithelial cell of stratified squamous epithelium of cornea tongue, oral cavity,
esophagus, anal canal, distal urethra, vagina
basal cell of these epithelia
cell of urinary epithelium Epithelial Cells Specialized for Exocrine Secretion cells of salivary gland
   mucous cell
   serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of a apocrine sweat gland
cell of gland of Moll in eyelid
cell of sebaceous gland, secreting lipid-rich sebum
cell of Bowman's gland in nose
cell of Brunner's gland in duodenum, secreting alkaline solution of mucus and enzymes
cell of seminal vesicle, secreting components of seminal fluid, including fructose
cell of prostate gland, secreting other components of seminal fluid
cell of bulbourethral gland, secreting mucus
cell of Bartholin's gland, secreting vaginal lubricant
cell of gland of Littré, secreting mucus
cell of endometrium of uterus, secreting mainly carbohydrates
isolated goblet cell of respiratory and digestive tracts, secreting mucus TABLE 2-continued Examples of Target Cells mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung
Cells Specialized for Secretion of Hormones cells of anterior pituitary, secreting
   growth hormone
   follicle-stimulating hormone
   luteinizing hormone
   prolactin
   adrenocorticotropic hormone
   thyroid-stimulating hormone
cell of intermediate pituitary, secreting melanocyte-stimulating hormone
cells of posterior pituitary, secreting
   oxytocin
   vasopressin
cells of gut and respiratory tract, secreting
   serotonin
   endorphin
   somatostatin
   gastrin
   secretin
   cholecystokinin
   insulin
   glucagons
   bombesin
cells of thyroid gland, secreting
   thyroid hormone
   calcitonin
cells of parathyroid gland, secreting
   parathyroid hormone
   oxyphil cell
cells of adrenal gland, secreting
   epinephrine
   norepinephrine
   steroid hormones
      mineralocorticoids
      glucocorticoids
cells of gonads, secreting
   testosterone
   estrogen
   progesterone
cells of juxtaglomerular apparatus of kidney
   juxtaglomerular cell
   macula densa cell
   peripolar cell
   mesangial cell
Epithelial Absorptive Cells in Gut, Exocrine Glands, and Urogenital Tract brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage hepatocyte
fat cells (e.g., adipocyte)
   white fat
   brown fat
   lipocyte of liver
Epithelial Cells Serving Primarily a Barrier
Function, Lining the Lung, Gut,
Exocrine Glands, and Urogenital Tract type I pneumocyte
pancreatic duct cell
nonstriated duct cell of sweat gland, salivary gland, mammary gland, etc.
parietal cell of kidney glomerulus
podocyte of kidney glomerulus TABLE 2-continued Examples of Target Cells cell of thin segment of loop of Henle
collecting duct cell
duct cell of seminal vesicle, prostate gland, etc.
Epithelial Cells Lining Closed Internal Body Cavities vascular endothelial cells of blood vessels and
lymphatics (e.g., microvascular cell)
   fenestrated
   continuous
   splenic
synovial cell
serosal cell
squamous cell lining perilymphatic space of ear
cells lining endolymphatic space of ear
   squamous cell
   columnar cells of endolymphatic sac
      with microvilli
      without microvilli
   "dark" cell
   vestibular membrane cell
   stria vascularis basal cell
   stria vascularis marginal cell
   cell of Claudius
   cell of Boettcher
choroid plexus cell
squamous cell of pia-arachnoid
cells of ciliary epithelium of eye
   pigmented
   nonpigmented
corneal "endothelial" cell
Ciliated Cells with Propulsive Function of respiratory tract
of oviduct and of endometrium of uterus
of rete testis and ductulus efferens
of central nervous system
Cells Specialized for Secretion of Extracellular Matrix epithelial:
   ameloblast
   planum semilunatum cell of vestibular apparatus of ear
   interdental cell of organ of Corti
nonepithelial:
   fibroblasts
   pericyte of blood capillary (Rouget cell)
   nucleus pulposus cell of intervertebral disc
   cementoblast/cementocyte
   odontoblast/odontocyte
   chondrocytes
      of hyaline cartilage
      of fibrocartilage
      of elastic cartilage
   osteoblast/osteocyte
   osteoprogenitor cell
   hyalocyte of vitreous body of eye
   stellate cell of perilymphatic space of ear
Contractile Cells skeletal muscle cells
   red
   white
   intermediate
   muscle spindle-nuclear bag
   muscle spindle-nuclear chain
   satellite cell
heart muscle cells
   ordinary
   nodal
   Purkinje fiber
   Cardiac valve tissue
smooth muscle cells
myoepithelial cells:
   of iris
   of exocrine glands
Cells of Blood and Immune System red blood cell (erythrocyte)
megakaryocyte TABLE 2-continued Examples of Target Cells macrophages
   monocyte
   connective tissue macrophage
   Langerhan's cell
   osteoclast
   dendritic cell
   microglial cell
neutrophil
eosinophil
basophil
mast cell
plasma cell
T lymphocyte
   helper T cell
   suppressor T cell
   killer T cell
B lymphocyte
   IgM
   IgG
   IgA
   IgE
killer cell
stem cells and committed progenitors for the blood and immune system
Sensory Transducers photoreceptors
   rod
   cones
      blue sensitive
      green sensitive
      red sensitive
hearing
   inner hair cell of organ of Corti
   outer hair cell of organ of Corti
acceleration and gravity
   type I hair cell of vestibular apparatus of ear
   type II hair cell of vestibular apparatus of ear
taste
   type II taste bud cell
smell
   olfactory neuron
   basal cell of olfactory epithelium
blood pH
   carotid body cell
      type I
      type II
touch
   Merkel cell of epidermis
   primary sensory neurons specialized for touch
temperature
   primary sensory neurons specialized for temperature
      cold sensitive
      heat sensitive
pain
   primary sensory neurons specialized for pain
configurations and forces in musculoskeletal system
   proprioceptive primary sensory neurons
Autonomic Neurons cholinergic
adrenergic
peptidergic
Supporting Cells of Sense Organs and of Peripheral Neurons supporting cells of organ of Corti
   inner pillar cell
   outer pillar cell
   inner phalangeal cell
   outer phalangeal cell
   border cell
   Hensen cell
supporting cell of vestibular apparatus
supporting cell of taste bud
supporting cell of olfactory epithelium
Schwann cell
satellite cell
enteric glial cell TABLE 2-continued Examples of Target Cells Neurons and Glial Cells of Central Nervous System neurons
glial cells
   astrocyte
   oligodendrocyte
Lens Cells anterior lens epithelial cell
lens fiber
Pigment Cells melanocyte
retinal pigmented epithelial cell
iris pigment epithelial cell
Germ Cells oogonium/oocyte
spermatocyte
Spermatogonium
blast cells
fertilized ovum
Nurse Cells ovarian follicle cell
Sertoli cell
thymus epithelial cell (e.g., reticular cell)
placental cell

EXAMPLE 7

Scaffold Swelling Study

Figure 19:
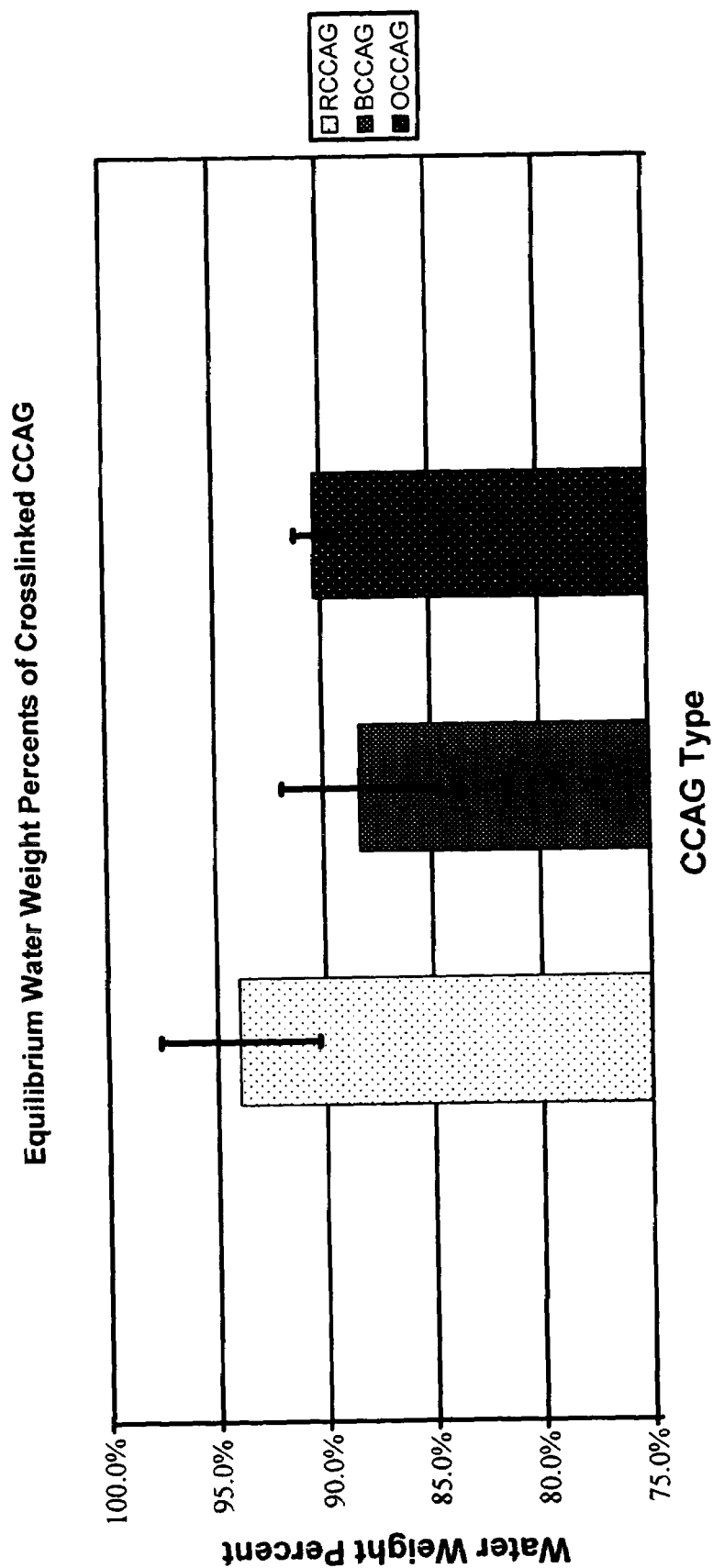
FIG. 19 is a graph showing equilibrium water weight percents of different CCAG derivatives.

FIG. 19 shows the results of the small swelling study comparing the different CCAG crosslinking methods. Although the graph suggests that raw CCAG contains the highest equilibrium water weight percent followed by oligochitosan stabilized CCAG and then barium stabilized CCAG, no significant differences between the groups were indicated by ANOVA analysis. The study should be repeated with larger sample sizes and a revised experimental procedure. The procedure implemented for wet sample weight measurement in this experiment was the largest source of systematic error.

Five small, previously washed samples from each material, RCCAG, BCCAG and OCCAG, were equilibrated in a minimum of DI water in 50 ml conical centrifuge tubes for at least a week. After equilibration, the samples were removed from the water, blotted to dryness on a Kimwipe, placed in a pre-weighed 15 ml conical centrifuge tube, weighed and recorded. The samples were then re-submerged in a minimum of DI water and flash frozen in liquid nitrogen. The frozen samples were then lyophilized for 48 hours. After lyophilization, the tubes w/sample were re-weighed and recorded. The difference between the initial weight and final weight was found for each sample and attributed solely to the loss of water during sample drying.

It should be understood that the examples and embodiments described herein are for illustrative purposes only and that various modifications or changes in light thereof will be suggested to persons skilled in the art and are to be included within the spirit and purview of this application.

We claim:

1. A biomaterial scaffold comprising an alginate gel and at least one stabilizing agent; wherein the alginate gel comprises a plurality of continuous parallel microtubular copper capillaries having a first end and a second end; and wherein the at least one stabilizing agent cross-links the alginate gel; and wherein the capillaries permit cell migration into the scaffold; and wherein the at least one stabilizing agent comprises a carbodiimide.

2. The biomaterial scaffold according to claim 1, wherein the diameter of each of the continuous parallel microtubular capillaries is within the range of about 10 μm to about 300 μm.

3. The biomaterial scaffold according to claim 1, wherein the diameters of each of the continuous parallel microtubular copper capillaries may be different; and wherein any one diameter may vary between the first end and the second end.

4. The biomaterial scaffold according to claim 1, wherein the cross-section of each of the continuous parallel microtubular copper capillaries is non-circular.

5. The biomaterial scaffold according to claim 1, wherein the biomaterial scaffold possesses a positive charge.

6. The biomaterial scaffold according to claim 1, further comprising at least one biologically active agent.

7. The biomaterial scaffold according to claim 1, further comprising at least one biologically active agent, and wherein the at least one biologically active agent comprises a plurality of cells seeded within the continuous parallel microtubular copper capillaries.

8. The biomaterial scaffold according to claim 7, wherein the plurality of cells are selected from the group consisting of embryonic stem cells, adult stem cells, blast cells, cloned cells, fertilized ova, placental cells, keratinocytes, basal epidermal cells, hair shaft cells, hair-root sheath cells, surface epithelial cells, basal epithelial cells, urinary epithelial cells, salivary gland cells, mucous cells, serous cells, von Ebner's gland cells, mammary gland cells, lacrimal gland cells, ceruminous gland cells, eccrine sweat gland cells, apocrine sweat gland cells, Moll gland cells, sebaceous gland cells, Bowman's gland cells, Brunner's gland cells, seminal vesicle cells, prostate gland cells, bulbourethral gland cells, Bartholin's gland cells, Littré gland cells, uterine endometrial cells, goblet cells of the respiratory or digestive tracts, mucous cells of the stomach, zymogenic cells of the gastric gland, oxyntic cells of the gastric gland, insulin-producing β cells, glucagon-producing α cells, somatostatin-producing δ cells, pancreatic polypeptide-producing cells, pancreatic ductal cells, Paneth cells of the small intestine, type II pneumocytes of the lung, Clara cells of the lung, anterior pituitary cells, intermediate pituitary cells, posterior pituitary cells, hormone secreting cells of the gut or respiratory tract, thyroid gland cells, parathyroid gland cells, adrenal gland cells, gonad cells, juxtaglomerular cells of the kidney, macula densa cells of the kidney, peripolar cells of the kidney, mesangial cells of the kidney, brush border cells of the intestine, striated duct cells of exocrine glands, gall bladder epithelial cells, brush border cells of the proximal tubule of the kidney, distal tubule cells of the kidney, nonciliated cells of ductulus efferens, epidydimal principal cells, epididymal basal cells, hepatacytes, fat cells, type I pneumocytes, pancreatic duct cells, nonstriated duct cells of the sweat gland, nonstriated duct cells of the salivary gland, nonstriated duct cells of the mammary gland, parietal cells of the kidney glomerulus, podocytes of the kidney glomerulus, cells of the thin segment of the loop of Henle, collecting duct cells, duct cells of the seminal vesicle, duct cells of the prostate gland, vascular endothelial cells, synovial cells, serosal cells, squamous cells lining the perilymphatic space of the ear, cells lining the endolymphatic space of the ear, choroids plexus cells, squamous cells of the pia-arachnoid, ciliary epithelial cells of the eye, corneal endothelial cells, ciliated cells having propulsive function, ameloblasts, planum semilunatum cells of the vestibular apparatus of the ear, interdental cells of the organ of Corti, fibroblasts, pericytes of blood capillaries, nucleus pulposus cells of the intervertebral disc, cementoblasts, cementocytes, odontoblasts, odontocytes, chondrocytes, osteoblasts, osteocytes, osteoprogenitor cells, hyalocytes of the vitreous body of the eye, stellate cells of the perilymphatic space of the ear, skeletal muscle cells, heart muscle cells, smooth muscle cells, myoepithelial cells, red blood cells, megakaryocytes, monocytes, connective tissue macrophages, Langerhan's cells, osteoclasts, dendritic cells, microglial cells, neutrophils, eosinophils, basophils, mast cells, plasma cells, helper T cells, suppressor T cells, killer T cells, immunoglobulin M, immunoglobulin G, immunoglobulin A, immunoglobulin E, killer cells, rod cells, cone cells, inner hair cells of the organ of Corti, outer hair cells of the organ of Corti, type I hair cells of the vestibular apparatus of the ear, type II cells of the vestibular apparatus of the ear, type II taste bud cells, olfactory neurons, basal cells of olfactory epithelium, type I carotid body cells, type Ii carotid body cells, Merkel cells, primary sensory neurons specialized for touch, primary sensory neurons specialized for temperature, primary neurons specialized for pain, proprioceptive primary sensory neurons, cholinergic neurons of the autonomic nervous system, adrenergic neurons of the autonomic nervous system, peptidergic neurons of the autonomic nervous system, inner pillar cells of the organ of Corti, outer pillar cells of the organ of Corti, inner phalangeal cells of the organ of Corti, outer phalangeal cells of the organ of Corti, border cells, Hensen cells, supporting cells of the vestibular apparatus, supporting cells of the taste bud, supporting cells of olfactory epithelium, Schwann cells, satellite cells, enteric glial cells, neurons of the central nervous system, astrocytes of the central nervous system, oligodendrocytes of the central nervous system, anterior lens epithelial cells, lens fiber cells, melanocytes, retinal pigmented epithelial cells, iris pigment epithelial cells, oogonium, oocytes, spermatocytes, spermatogonium, ovarian follicle cells, Sertoli cells, and thymus epithelial cells, or combinations thereof.

9. The biomaterial scaffold according to claim 1, wherein said carbodiimide is N-ethyl-N'-(3-dimethylaminopropyl)-carbodiimide, NN'-dicyclohexyl-carbodiimide (DCC), N'-diisopropyl-carbodiimide, N'N'-di-tert-butylcarbodiimide, 1-cyclo-hexyl-3-(4-diethylaminocyclohexyl)carbodiimide, 1,3-di-(4-diethylaminocyclo-hexyl)carbodiimide, 1-cyclohexyl-3-(-diethylaminoethylcarbodiimide, 1-cyclohexyl-1-cyclohexyl-3-(2-morphonlinyl-(4)-ethyl)carbodiimide, or 1-cyclohexyl-3-(4-diethyl-aminocyclohexyl)carbodiimide.

10. The biomaterial scaffold according to claim 1, wherein the scaffold is non-toxic to living cells.

11. The biomaterial scaffold according to claim 1, wherein the diameter of each of the continuous parallel microtubular capillaries is within the range of about 10 μm to about 250 μm.

12. The biomaterial scaffold according to claim 1, wherein the diameter of each of the continuous parallel microtubular capillaries is within the range of about 25μm to about 30 μm.

13. The biomaterial scaffold according to claim 1, wherein the scaffold comprises a particle or bioglass.

14. A biomaterial scaffold comprising an alginate gel and at least one stabilizing agent; wherein the alginate gel comprises a plurality of continuous parallel microtubular copper capillaries having a first end and a second end; and wherein the at least one stabilizing agent cross-links the alginate gel; and wherein the capillaries permit cell migration into the scaffold; and further comprising at least one biologically active agent, and wherein the at least one biologically active agent comprises a plurality of cells seeded within the continuous parallel microtubular copper capillaries.

15. The biomaterial scaffold according to claim 14, wherein the at least one stabilizing agent is divalent cations, an electrostatically charged molecule, a polysaccharide, or a carbodiimide.

16. The biomaterial scaffold according to claim 14, wherein the at least one stabilizing agent comprises a barium cation.

17. The biomaterial scaffold according to claim 15, wherein the electrostatically charged molecule is selected from the group consisting of chitosan, chitosan derivatives, oligochitosan, and poly-lysine, or any combination of the foregoing.

18. The biomaterial scaffold according to claim 14, wherein the diameter of each of the continuous parallel microtubular capillaries is within the range of about 10 μm to about 300 μm.

19. The biomaterial scaffold according to claim 14, wherein the diameters of each of the continuous parallel microtubular copper capillaries may be different; and wherein any one diameter may vary between the first end and the second end.

20. The biomaterial scaffold according to claim 14, wherein the cross-section of each of the continuous parallel microtubular copper capillaries is non-circular.

21. The biomaterial scaffold according to claim 14, wherein the biomaterial scaffold possesses a positive charge.

22. The biomaterial scaffold according to claim 14, wherein the plurality of cells are selected from the group consisting of embryonic stem cells, adult stem cells, blast cells, cloned cells, fertilized ova, placental cells, keratinocytes, basal epidermal cells, hair shaft cells, hair-root sheath cells, surface epithelial cells, basal epithelial cells, urinary epithelial cells, salivary gland cells, mucous cells, serous cells, von Ebner's gland cells, mammary gland cells, lacrimal gland cells, ceruminous gland cells, eccrine sweat gland cells, apocrine sweat gland cells, Moll gland cells, sebaceous gland cells, Bowman's gland cells, Brunner's gland cells, seminal vesicle cells, prostate gland cells, bulbourethral gland cells, Bartholin's gland cells, Littré gland cells, uterine endometrial cells, goblet cells of the respiratory or digestive tracts, mucous cells of the stomach, zymogenic cells of the gastric gland, oxyntic cells of the gastric gland, insulin-producing β cells, glucagon-producing α cells, somatostatin-producing δ cells, pancreatic polypeptide-producing cells, pancreatic ductal cells, Paneth cells of the small intestine, type II pneumocytes of the lung, Clara cells of the lung, anterior pituitary cells, intermediate pituitary cells, posterior pituitary cells, hormone secreting cells of the gut or respiratory tract, thyroid gland cells, parathyroid gland cells, adrenal gland cells, gonad cells, juxtaglomerular cells of the kidney, macula densa cells of the kidney, peripolar cells of the kidney, mesangial cells of the kidney, brush border cells of the intestine, striated duct cells of exocrine glands, gall bladder epithelial cells, brush border cells of the proximal tubule of the kidney, distal tubule cells of the kidney, nonciliated cells of ductulus efferens, epididymal principal cells, epididymal basal cells, hepatacytes, fat cells, type I pneumocytes, pancreatic duct cells, nonstriated duct cells of the sweat gland, nonstriated duct cells of the salivary gland, nonstriated duct cells of the mammary gland, parietal cells of the kidney glomerulus, podocytes of the kidney glomerulus, cells of the thin segment of the loop of Henle, collecting duct cells, duct cells of the seminal vesicle, duct cells of the prostate gland, vascular endothelial cells, synovial cells, serosal cells, squamous cells lining the perilymphatic space of the ear, cells lining the endolymphatic space of the ear, choroids plexus cells, squamous cells of the pia-arachnoid, ciliary epithelial cells of the eye, corneal endothelial cells, ciliated cells having propulsive function, ameloblasts, planum semilunatum cells of the vestibular apparatus of the ear, interdental cells of the organ of Corti, fibroblasts, pericytes of blood capillaries, nucleus pulposus cells of the intervertebral disc, cementoblasts, cementocytes, odontoblasts, odontocytes, chondrocytes, osteoblasts, osteocytes, osteoprogenitor cells, hyalocytes of the vitreous body of the eye, stellate cells of the perilymphatic space of the ear, skeletal muscle cells, heart muscle cells, smooth muscle cells, myoepithelial cells, red blood cells, megakaryocytes, monocytes, connective tissue macrophages, Langerhan's cells, osteoclasts, dendritic cells, microglial cells, neutrophils, eosinophils, basophils, mast cells, plasma cells, helper T cells, suppressor T cells, killer T cells, immunoglobulin M, immunoglobulin G, immunoglobulin A, immunoglobulin F, killer cells, rod cells, cone cells, inner hair cells of the organ of Corti, outer hair cells of the organ of Corti, type I hair cells of the vestibular apparatus of the ear, type II cells of the vestibular apparatus of the ear, type II taste bud cells, olfactory neurons, basal cells of olfactory epithelium, type I carotid body cells, type II carotid body cells, Merkel cells, primary sensory neurons specialized for touch, primary sensory neurons specialized for temperature, primary neurons specialized for pain, proprioceptive primary sensory neurons, cholinergic neurons of the autonomic nervous system, adrenergic neurons of the autonomic nervous system, peptidergic neurons of the autonomic nervous system, inner pillar cells of the organ of Corti, outer pillar cells of the organ of Corti, inner phalangeal cells of the organ of Corti, outer phalangeal cells of the organ of Corti, border cells, Hensen cells, supporting cells of the vestibular apparatus, supporting cells of the taste bud, supporting cells of olfactory epithelium, Schwann cells, satellite cells, enteric glial cells, neurons of the central nervous system, astrocytes of the central nervous system, oligodendrocytes of the central nervous system, anterior lens epithelial cells, lens fiber cells, melanocytes, retinal pigmented epithelial cells, iris pigment epithelial cells, oogonium, oocytes, spermatocytes, spermatogonium, ovarian follicle cells, Sertoli cells, and thymus epithelial cells, or combinations thereof.

23. The biomaterial scaffold according to claim 14, wherein the at least one stabilizing agent includes at least one of: $Cd^{++}$, $Cu^{++}$, $Ca^{++}$, $Ni^{++}$, $Co^{++}$, or $Mn^{++}$.

24. The biomaterial scaffold according to claim 15, wherein said carbodiimide is N-ethyl-N'-(3-dimethylaminopropyl)-carbodiimide, NN'-dicyclohexyl-carbodiimide (DCC), N'-diisopropyl-carbodiimide, N'N'-di-tert-butylcarbodiimide, 1-cyclo-hexyl-3-(4-diethylaminocyclohexyl)carbodiimide, 1,3-di-(4-diethylaminocyclo-hexyl)carbodiimide, 1-cyclohexyl-3-(-diethylaminoethylcarbodiimide, 1-cyclohexyl-1-cyclohexyl-3-(2-morphonlinyl-(4)-ethyl) carbodiimide, or 1-cyclohexyl-3-(4-diethyl-aminocyclohexyl)carbodiimide.

25. The biomaterial scaffold according to claim 14, wherein the at least one stabilizing agent comprises a divalent cation and an electrostatically charged molecule, to form a polyelectrolyte complex (PEC).

26. The biomaterial scaffold according to claim 25, comprising multiple layers of the PEC.

27. The biomaterial scaffold according to claim 14, wherein the scaffold is non-toxic to living cells.

28. The biomaterial scaffold according to claim 14, wherein the diameter of each of the continuous parallel microtubular capillaries is within the range of about 10 μm to about 250 μm.

29. The biomaterial scaffold according to claim 14, wherein the diameter of each of the continuous parallel microtubular capillaries is within the range of about 25 μm to about 30 μm.

30. The biomaterial scaffold according to claim 14, wherein the scaffold comprises a particle or bioglass.

31. The biomaterial scaffold according to claim 14, wherein the at least one stabilizing agent is a carbodiimide.

\* \* \* \* \*

UNITED STATES PATENT AND TRADEMARK OFFICE
CERTIFICATE OF CORRECTION

PATENT NO. : 7,601,525 B2 Page 1 of 1
APPLICATION NO. : 11/074285
DATED : October 13, 2009
INVENTOR(S) : Christopher Batich et al.

It is certified that error appears in the above-identified patent and that said Letters Patent is hereby corrected as shown below:

Column 30,
Line 14, "type Ii" should read --type II--.

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,525 B2 | Page 1 of 1 |
| APPLICATION NO. | : 11/074285 | |
| DATED | : October 13, 2009 | |
| INVENTOR(S) | : Batich et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Fifth Day of October, 2010

David J. Kappos
*Director of the United States Patent and Trademark Office*